United States Patent
Fliri et al.

(10) Patent No.: US 6,531,468 B2
(45) Date of Patent: Mar. 11, 2003

(54) DIAZABICYCLOOCTANE DERIVATIVES AND THERAPEUTIC USES THEREOF

(75) Inventors: Anton Franz Joseph Fliri, Stonington, CT (US); Randall James Gallaschun, Lebanon, CT (US)

(73) Assignee: Pfizer Inc, New York, NY (US)

(*) Notice: Subject to any disclaimer, the term of this patent is extended or adjusted under 35 U.S.C. 154(b) by 0 days.

(21) Appl. No.: 09/920,587

(22) Filed: Aug. 1, 2001

(65) Prior Publication Data

US 2002/0068748 A1 Jun. 6, 2002

Related U.S. Application Data

(60) Provisional application No. 60/222,706, filed on Aug. 3, 2000.

(51) Int. Cl.[7] .................... C07D 487/08; A61K 31/495; A61P 25/00
(52) U.S. Cl. ......................... 514/214.03; 514/253.04; 540/582; 540/583; 540/584; 544/362
(58) Field of Search ................ 540/582, 583, 540/584; 514/214.03, 253.04; 544/362

(56) References Cited

U.S. PATENT DOCUMENTS 3,951,980 A  4/1976  Henry et al. ............ 260/268

FOREIGN PATENT DOCUMENTS

FR   2531709   2/1984

*Primary Examiner*—Bruck Kifle
(74) *Attorney, Agent, or Firm*—Peter C. Richardson; Paul H. Ginsburg; A. David Joran

(57) ABSTRACT

The present invention provides diazabicyclooctane derivatives of formula (I):

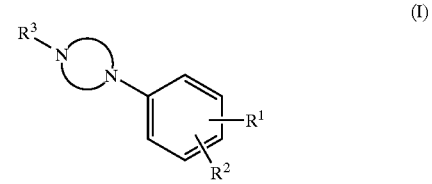

(I)

and pharmaceutically acceptable salts thereof, wherein the group represents

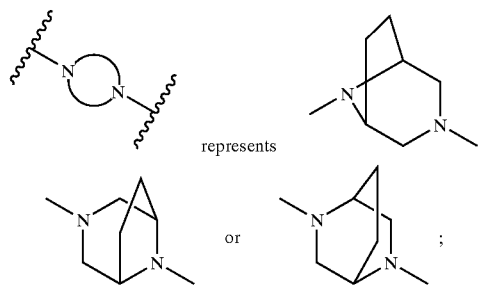

$R^1$ and $R^2$ are selected independently from H, ($C_1$–$C_6$) alkyl, ($C_1$–$C_6$)fluoroalkyl, halogen (e.g., F. Cl, Br, I), cyano, nitro, O—($C_1$–$C_6$)alkyl, O—($C_1$–$C_6$) fluoroalkyl, —NHC(O)$R^4$ and —O$R^4$, where $R^4$ and $R^5$ are selected independently from H, ($C_1$–$C_6$)alkyl, and a 5- to 7-membered aryl or heteroaryl ring, or $R^1$ and $R^2$ together with the atoms to which they are attached, form a carbocyclic 5- or 6-membered ring or a heterocyclic 5- or 6-membered ring; and $R^3$ is selected from the group consisting of H, ($C_1$–$C_6$) alkyl, $(CH_2)_m$-aryl or $(CH_2)_m$-heteroaryl, wherein m is an integer from 1 to 4, each aryl or heteroaryl group optionally substituted with Cl, Br, CN, $CF_3$, O—($C_1$–$C_6$)alkyl, ($C_1$–$C_6$)alkyl, sulfonyl($C_1$–$C_6$)alkyl, —CO($C_1$–$C_6$)alkyl, —$CONH_2$, —CONH($C_1$–$C_6$) alkyl, —CON(($C_1$–$C_6$)alkyl)$_2$, or CH(OH)($C_1$–$C_6$) alkyl.

The invention also relates to pharmaceutical compositions of a compound of formula (I), and methods of use thereof in the treatment of diseases, conditions or disorders of the central nervous system. Further, the present invention is also directed to processes for the preparation of compounds of formula (I) and intermediates useful therefor.

12 Claims, No Drawings

# DIAZABICYCLOOCTANE DERIVATIVES AND THERAPEUTIC USES THEREOF

This application claims the benefit of U.S. provisional application Ser. No. 60/222,706, filed Aug. 3, 2000.

The present invention is directed to diazabicyclooctane derivatives and pharmaceutically acceptable salts thereof, to pharmaceutical compositions thereof, and to the use thereof to block selectively serotonin reuptake in the central nervous system of a mammal. The present invention is also directed to the use of the diazabicyclooctane derivatives of the invention in a method for the treatment of various diseases, disorders and conditions of the central nervous system. Further, the present invention is directed to processes for the preparation of diazabicyclooctane derivatives and intermediates useful therein.

Serotonin (5-hydroxytryptamine, "5-HT") is a monoamine neurotransmitter active in the central nervous systems of mammals, including humans. The cell bodies of serotoninergic cells are located in the brain stem, and the axons project therefrom into a variety of other areas, e.g., the amygdala, hippocampus, hypothalamus, nucleus accumbens and the striatum. Serotonin-producing cells store the neurotransmitter in intracellular vesicles, where it is either converted with monoamine oxidase ("MAO" EC 1.4.3.4) into 5-hydroxyindoleacetic acid ("5-HIAA") or released into synapses. In the synapses, serotonin is either resorbed into the presynaptic neurons and stored within intracellular vesicles of the presynaptic neurons or remains available for interaction with serotonin receptors, e.g., the $5-HT_{2A}$ receptor, in post-synaptic membranes.

Altered functioning of this serotonin-based neurotransmission system has been implicated (see, e.g., Lancet, 2: 717–719 (1989)) in a variety of central nervous system related disorders, both psychiatric and non-psychiatric. These disorders include, without limitation, schizophrenia, psychosis, depression, aggression, sleep disorders, anxiety disorders, migraines, compulsive disorders, bipolar disorders, vision disorders, emesis, feeding disorders, learning disorders, sexual behavior disorders, phobias and substance abuse disorders. Compounds that either block serotonin reuptake into presynaptic neurons or that antagonize its interaction with post-synaptic membrane receptors have a wide variety of potential applications in the treatment of mammals, including humans, afflicted with central nervous system related disorders. Such compounds act to restore some semblance of normal neurotransmitter functioning. Moreover, compounds which accomplish these objectives selectively can be used with a lower risk of attendant and unwanted side effects, e.g., sexual dysfunction, etc.

French Patent Application No. 2,531,709 A1 relates to pyrimidinyl diazabicyclo[3.2.1]octane derivatives with anxiolytic, hypnotic and sedative activity and discusses the synthesis of benzyl, phenyl and tolyl derivatives of diazabicyclo[3.2.1]octane. Occelli et al., Farmaco Ed. Sci, 32(4), pp. 237–47 (1977) discusses the anti-Parkinson activity of 3,8-diazabicyclo[3.2.1]octanes. Fontanella et al., Farmaco Ed. Sci, 27(1), pp. 68–78 (1972) has noted the pharmacological activity of 3,8-diazabicyclo[3.2.1]octane-2,4-diones. Ghelardini et al. have discussed the antiamnesic activity of a diazabicyclo[3.2.1]octane nicotinic agonist, DBO-83, in mice in Drug Dev. Res., 45(2), pp. 45–51 (1998).

WO 99/11647 discusses the preparation of fused thiophene compounds as anti-psychotics. WO 96/13503 relates to certain tricyclic substituted diazabicyclo[3.2.1] octane derivatives useful as dopamine receptor ligands, and particularly as atypical anti-psychotics. U.S. Pat. No. 3,905,979 relates to a variety of diazabicyclooctane based diethylcarbamazine derivatives useful as bronchodilators and antifilarial agents and their synthetic preparation from diethyl meso-α,α'-dibromoadipate. German Patent No. 63-1595893 shows a series of 3,8-diazabicyclo[3.2.1]octane derivatives useful as analgesics. Czech patent application No. CS 70-5352 relates to the neuroleptic activity of 3,8-diazabicyclo[3.2.1]octane enamine derivatives of the dibenzo[b,f]thiepin series. Czech patent application No. 70-5354 relates to neuroleptic piperazine enamines derived from tricyclic skeletons. Jilek et al., Czech. Chem. Commun., 36(12), 4074 (1971) discussed the neurotropic and psychotropic activity of 3,8-diazabicyclo[3.2.1]octyl derivatives of dibenzo[b,f]thiepin. The synthesis and pharmacological properties of phenothiazine and 10,11-dihydrodibenzocycloheptene derivatives of 3,8-diazabicyclo[3.2.1]octanes are discussed in Cignarella et al., J. Med. Chem., 12(5), 836–9 (1969). The synthesis of disubstituted 3,8-diazabicyclo[3.2.1]octane derivatives and the use of these compounds as local anesthetics and spasmolytics are discussed in U.S. Pat. No. 3,328,396. WO 93/25527 relates to piperidine, tetrahydropyridine and piperazine derivatives as nervous system agents.

Japanese Kokai No. 63-098662 relates to the use of substituted 3,8-diazabicyclo[3:2:1]octane derivatives as photographic photosensitive materials. U.S. Pat. Nos. 4,018,895, 4,194,009, 4,314,081 and 5,026,707 discuss potent inhibitors of the uptake of various physiologically active monoamines, including serotonin, norepinephrine and dopamine. Certain 8-methyl-3-aryl-8-azabicyclo[3.2.1]-2-enes have been reported to possess useful monoamine neurotransmitter reuptake inhibition activity in International Patent publication No. WO 97/13770. The monoamine uptake inhibition activity of tropane derivatives: 8-azabicyclo[3.2.1]-2-enes and 8-azabicyclo[3.2.1]-2-anes has been discussed in European Application Nos. EP 0 969 005, EP 0 859 777, EP 0 944 626, EP 0 929 319, and EP 0 604354; U.S. Pat. Nos. 5,922,732 and 5,980,860; and International Patent publication Nos. WO 92/22554, WO 94/04146.

European Application No. 0 952 154 discusses diazabicyclo[2.2.1]heptane derivatives as 5HT1 agonists or antagonist. International Patent publication No. WO 98/50030 discusses diazabicyclo[2.2.1]heptane derivatives as inhibitors of protein isoprenyl transferases. International Patent publication No. WO 97/40049 discusses diazabicyclo [2.2.1]heptane derivatives as inhibitors of acetylcholinesterases useful for treatment of dementia and Alzheimer's disease. U.S. Pat. No. 5,478,939 discusses (R,R)- and (S,S)-2,5-diazabicyclo[2.2.1]heptane derivatives as muscarinic agonists. European Patent Application No. 0 324 543 discusses bridged diazabicyclo[2.2.1]heptane derivatives as antiarrhythmic agents. International Patent publication No. WO 97/26258 discusses angiogenesis inhibiting pyridazinamines containing bridged diazabicyclo[2.2.2]octane derivatives. Japanese Kokai No. 09-020758 discusses piperazinylbutyronitrile derivatives containing a bridged diazabicyclo[2.2.2]octane structure element as muscarinic antagonists.

U.S. Pat. No. 5,382,584 and European Patent Application No. 0 582 164 discuss adenosine re-uptake inhibiting diphenyl oxazoles, thiazoles and imidazoles derivatives containing a bridged diazabicyclo[2.2.2]octane structure element. U.S. Pat. Nos. 3,951,980 and 3,947,445; and J. Med. Chem., 17(5), pp. 481–7 (1974) discuss carbamazine derivatives useful as bronchodilators and antifilarial agents containing diazabicyclooctane and diazabicycloheptane substructures. *J. Org. Chem.*, 36(22), pp. 3361–5 (1971) reports on the synthesis of 2,5-diphenyl-2,5-diazabicyclo[2.2.2]-octane.

However, none of these documents teach or suggest either the serotonin, dopamine and norepinephrine reuptake inhibitory activity of diazabicyclo[3.2.1], and diazabicyclo[2.2.2} compounds of the present invention or the therapeutic uses of the present invention.

SUMMARY OF THE INVENTION

The present invention provides compounds of formula (I):

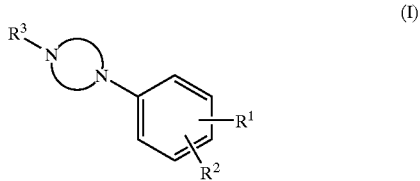

(I)

and pharmaceutically acceptable salts thereof, wherein the group

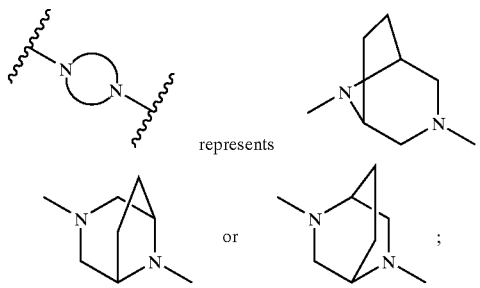

represents or

;

$R^1$ and $R^2$ are selected independently from H, $(C_1-C_6)$ alkyl, $(C_1-C_6)$fluoroalkyl, halogen (e.g., F, Cl, Br, I), cyano, nitro, O—$(C_1-C_6)$alkyl, O—$(C_1-C_6)$ fluoroalkyl, —NHC(O)$R^4$ and —O$R^5$, where $R^4$ and $R^5$ are selected independently from H, $(C_1-C_6)$alkyl, and a 5- to 7-membered aryl or heteroaryl ring, or $R^1$ and $R^2$ together with the atoms to which they are attached, form a carbocyclic 5- or 6-membered ring or a heterocyclic 5- or 6-membered ring; and $R^3$ is selected from the group consisting of H, $(C_1-C_6)$ alkyl, $(CH_2)_m$-aryl or $(CH_2)_m$-heteroaryl, wherein m is an integer from 1 to 4, each aryl or heteroaryl group optionally substituted with Cl, Br, CN, $CF_3$, O—$(C_1-C_6)$alkyl, $(C_1-C_6)$alkyl, sulfonyl$(C_1-C_6)$alkyl, —CO$(C_1-C_6)$alkyl, —CONH$_2$, —CONH$(C_1-C_6)$ alkyl, —CON$((C_1-C_6)$alkyl$)_2$, or CH(OH)$(C_1-C_6)$ alkyl, with the proviso that neither $R^1$ nor $R^2$ can be H or methyl, when $R^3$ is H, phenyl or —$(CH_2)_m$-phenyl.

Preferred compounds of the invention are those of formula (I) wherein

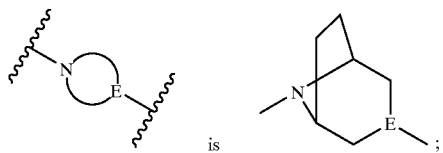

is

;

$R^3$ is H or $(C_1-C_6)$alkyl; and $R^1$ and $R^2$ are independently chosen from the group consisting of H, halogen, —$CF_3$, $(C_1-C_6)$alkyl, —OCH$_3$, and OCF$_3$.

The most preferred embodiments of the invention are those compounds of formula (I) wherein $R^3$ is H and $R^1$ and $R^2$ are independently chosen from the group consisting of Cl, —$CF_3$, $(C_1-C_6)$alkyl, —OCH$_3$, and OCF$_3$.

Specifically preferred embodiments of the invention are:
3-(4-chlorophenyl)-3,8-diazabicyclo[3.2.1]octane;
3-(3,4-dichlorophenyl)-3,8-diazabicyclo[3.2.1]octane;
3-(2,4-dimethylphenyl)-3,8-diazabicyclo[3.2.1]octane;
3-(4-fluorophenyl)-3,8-diazabicyclo[3.2.1]octane;
3-(4-trifluoromethylphenyl)-3,8-diazabicyclo[3.2.1] octane;
3-(3-fluorophenyl)-3,8-diazabicyclo[3.2.1]octane;
8-(4-chlorophenyl)-3,8-diazabicyclo[3.2.1]octane;
8-(p-tolyl)-3,8-diazabicyclo[3.2.1]octane; 3-(p-tolyl)-3,8-diazabicyclo[3.2.1]octane;
8-(3,4-dichlorophenyl)-3,8-diazabicyclo[3.2.1]octane;
8-phenyl-3,8-diazabicyclo[3.2.1]octane;
8-(2,4-dimethylphenyl)-3,8-diazabicyclo[3.2.1]octane;
8-(4-fluorophenyl)-3,8-diazabicyclo[3.2.1]octane;
8-(4-trifluoromethylphenyl)-3,8-diazabicyclo[3.2.1] octane;
8-(3-fluorophenyl)-3,8-diazabicyclo[3.2.1]octane;
8-benzyl-3-(4-fluorophenyl)-3,8-diaza-bicyclo[3.2.1] octane;
2-benzyl-5-(4-fluorophenyl)-2,5-diaza-bicyclo[2.2.2] octane;
8-benzyl-3-(4-chlorophenyl)-3,8-diaza-bicyclo[3.2.1] octane;
2-benzyl-5-(4-chlorophenyl)-2,5-diaza-bicyclo[2.2.2] octane;
8-ethyl-3-(4-chlorophenyl)-3,8-diaza-bicyclo[3.2.1] octane;
2-ethyl-5-(4-chlorophenyl)-2,5-diaza-bicyclo[2.2.2] octane;
8-methyl-3-(4-chlorophenyl)-3,8-diaza-bicyclo[3.2.1] octane;
2-methyl-5-(4-chlorophenyl)-2,5-diaza-bicyclo[2.2.2] octane;
8-ethyl-3-(3,4-dichlorophenyl)-3,8-diaza-bicyclo[3.2.1] octane;
2-ethyl-5-(3,4-dichlorophenyl)-2,5-diaza-bicyclo[2.2.2] octane;
8-methyl-3-(3,4-dichlorophenyl)-3,8-diaza-bicyclo [3.2.1]octane;
2-methyl-5-(3,4-dichlorophenyl)-2,5-diaza-bicyclo [2.2.2]octane;
8-ethyl-3-(4-methylphenyl)-3,8-diaza-bicyclo[3.2.1] octane;
2-ethyl-5-(4-methylphenyl)-2,5-diaza-bicyclo[2.2.2] octane;
8-methyl-3-(4-methylphenyl)-3,8-diaza-bicyclo[3.2.1] octane;
2-methyl-5-(4-methylphenyl)-2,5-diaza-bicyclo[2.2.2] octane;
3-benzyl-8-(4-chlorophenyl)-3,8-diaza-bicyclo[3.2.1] octane;
3-methyl-8-(4-chlorophenyl)-3,8-diaza-bicyclo[3.2.1] octane;
3-propyl-8-(4-chloro-phenyl)-3,8-diaza-bicyclo[3.2.1] octane;
3-(2-naphthyl)-3,8-diazabicyclo[3.2.1]octane;

3-(1-naphthyl)-3,8-diazabicyclo[3.2.1]octane;
3-(2-isoquinolyl)-3,8-diazabicyclo[3.2.1]octane
8-(2-naphthyl)-3,8-diazabicyclo[3.2.1]octane;
8-(1-naphthyl)-3,8-diazabicyclo[3.2.1]octane
8-(2-isoquinolyl)-3,8-diazabicyclo[3.2.1]octane
2-(4-chlorophenyl)-2,5-diaza-bicyclo[2.2.2]octane;
8-methyl-3-(3-trifluoromethylphenyl)-3,8-diazabicyclo[3.2.1]octane; and
2-(4-fluorophenyl)-2,5-diazabicyclo[2.2.2]octane and pharmaceutically acceptable salts thereof.

The present invention also provides a method for treating a disease, disorder or condition in a mammal that can be treated by inhibiting serotonin reuptake in the central nervous system of a mammal, comprising the administration to the mammal a serotonin reuptake-inhibiting effective amount of a compound of formula (I)

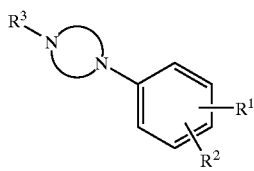

(I)

or a pharmaceutically acceptable salt thereof; wherein the group

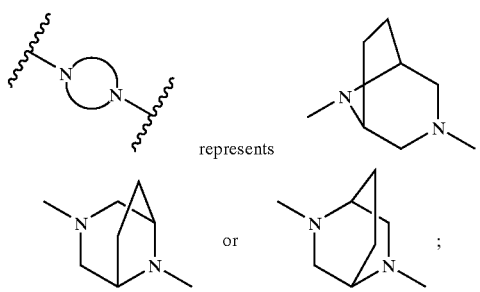

represents or a pharmaceutically acceptable salt thereof; wherein the group $R^1$ and $R^2$ are selected independently from H, $(C_1-C_6)$ alkyl, $(C_1-C_6)$fluoroalkyl, halogen (e.g., F, Cl, Br, I), cyano, nitro, O—$(C_1-C_6)$alkyl, O—$(C_1-C_6)$ fluoroalkyl, —NHC(O)$R^4$ and —O$R^5$, where $R^4$ and $R^5$ are selected independently from H, $(C_1-C_6)$alkyl, and a 5- to 7-membered aryl or heteroaryl ring, or $R^1$ and $R^2$ together with the atoms to which they are attached, form a carbocyclic 5- or 6-membered ring or a heterocyclic 5- or 6-membered ring; and $R^3$ is selected from the group consisting of H, $(C_1-C_6)$ alkyl, $(CH_2)_m$-aryl or $(CH_2)_m$-heteroaryl, wherein m is an integer from 1 to 4, each aryl or heteroaryl group optionally substituted with Cl, Br, CN, $CF_3$, O—$(C_1-C_6)$alkyl, $(C_1-C_6)$alkyl, sulfonyl$(C_1-C_6)$alkyl, —CO$(C_1-C_6)$alkyl, —$CONH_2$, —CONH$(C_1-C_6)$ alkyl, —CON$((C_1-C_6)$alkyl$)_2$, or CH(OH)$(C_1-C_6)$ alkyl.

The present invention further provides a method for treating a disease, disorder or condition in a mammal that can be treated by inhibiting serotonin reuptake in the central nervous system of a mammal, comprising the administration to the mammal an amount of a compound of formula (I)

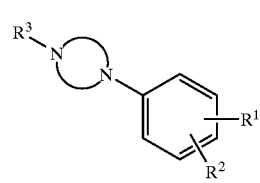

(I)

or a pharmaceutically acceptable salt thereof; wherein the group represents

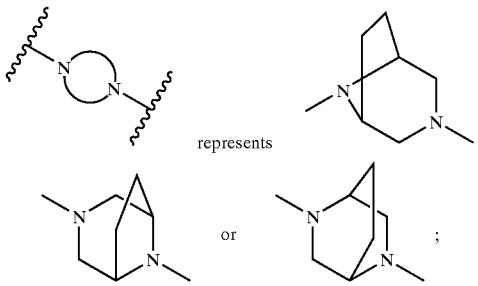

$R^1$ and $R^2$ are selected independently from H, $(C_1-C_6)$ alkyl, $(C_1-C_6)$fluoroalkyl, halogen (e.g., F, Cl, Br, I), cyano, nitro, O—$(C_1-C_6)$alkyl, O—$(C_1-C_6)$ fluoroalkyl, —NHC(O)$R^4$ and —O$R^5$, where $R^4$ and $R^5$ are selected independently from H, $(C_1-C_6)$alkyl, and a 5- to 7-membered aryl or heteroaryl ring, or $R^1$ and $R^2$ together with the atoms to which they are attached, form a carbocyclic 5- or 6-membered ring or a heterocyclic 5- or 6-membered ring; and $R^3$ is selected from the group consisting of H, $(C_1-C_6)$ alkyl, $(CH_2)_m$-aryl or $(CH_2)_m$-heteroaryl, wherein m is an integer from 1 to 4, each aryl or heteroaryl group optionally substituted with Cl, Br, CN, $CF_3$, O—$(C_1-C_6)$alkyl, $(C_1-C_6)$alkyl, sulfonyl$(C_1-C_6)$alkyl, —CO$(C_1-C_6)$alkyl, —$CONH_2$, —CONH$(C_1-C_6)$ alkyl, —CON$((C_1-C_6)$alkyl$)_2$, or CH(OH)$(C_1-C_6)$ alkyl; which is effective to treat the disease, disorder or condition.

The present invention further provides a method of treating in a mammal a disease, disorder or condition selected from the group consisting of aggression disorders; anxiety disorders (e.g., panic attack, agoraphobia, panic disorder with or without agoraphobia, agoraphobia without history of panic disorder, specific phobia, social phobia, obsessive-compulsive disorder, post-traumatic stress disorder and acute stress disorder); cognitive disorders selected from the group consisting of amnestic disorders (e.g., amnestic disorders due to a general medical condition, substance-induced persisting amnestic disorder and amnestic disorders not otherwise specified), deliriums (e.g., deliriums due to a general medical condition, substance-induced delirium and delirium not otherwise specified), dementias (e.g., dementia of the Alzheimer's type, vascular dementia, dementia due to a general medical condition (e.g., AIDS-, Parkinson's-, head trauma-, and Huntington's-induced dementias), substance-induced persisting dementia, dementia due to multiple etiologies, and dementia not otherwise specified) and cognitive disorders not otherwise specified; depression disorders; emesis; epilepsy; food-related behavioral disorders, including anorexia nervosa and bulimia; headache disorders selected from the group consisting of migraine, cluster and vascular headaches; learning disorders, including attention deficit disorder and attention deficit/hyperactivity disorder; obesity; ocular disorders; platelet aggregation disorders; psychotic conditions selected from the group consisting of schizophrenia (e.g., paranoid-type, disorganized-type, catatonic-type, undifferentiated-type and residual-type), schizophreniform disorder, schizoaffective disorder, delusional disorder, brief psychotic disorder, shared psychotic disorder, psychotic disorders due to a general medical condition and psychotic disorders not otherwise specified; sleep disorders selected from the group consisting of primary sleep disorders (e.g., parasomnias and dyssomnias), sleep disorders related to another mental disorder (including, without limitation, mood and anxiety disorders), sleep disorders due to a general medical condition and sleep disorders not otherwise specified; sexual behavior disorders; substance-abuse disorders selected from the group consisting of alcohol-related disorders, including alcohol-use disorders (e.g., dependence and abuse disorders) and alcohol-induced disorders (e.g., intoxication, withdrawal, intoxication delirium, withdrawal delirium, persisting dementia, persisting amnestic, mood, anxiety, sexual dysfunction, sleep and not otherwise specified disorders), amphetamine-related disorders, including amphetamine-use disorders (e.g., dependence and abuse disorders) and amphetamine-induced disorders (e.g., intoxication, withdrawal, intoxication delirium, psychotic, mood, anxiety, sexual dysfunction, sleep and not otherwise-specified disorders), caffeine-related disorders, such as intoxication, induced-anxiety disorder, induced-sleep disorder and disorders not otherwise specified; cannabis-related disorders, including cannabis-use disorders (e.g., abuse and dependence disorders) and cannabis-induced disorders (e.g., intoxication, intoxication delirium, psychotic, anxiety and not otherwise specified disorders), cocaine-related disorders, including cocaine-use disorders (e.g., dependence and abuse disorders) and cocaine-induced disorders (e.g., intoxication, withdrawal, intoxication delirium, psychotic, mood, anxiety, sexual dysfunction, sleep and not otherwise specified disorders), hallucinogen-related disorders, including hallucinogen-use disorders (e.g., dependence and abuse disorders) and hallucinogen-induced disorders (e.g., intoxication, persisting perception, intoxication delirium, psychotic, mood, anxiety and not otherwise specified disorders), inhalant-related disorders, including inhalant-use disorders (e.g., dependence and abuse disorders) and inhalant-induced disorders (e.g., intoxication, intoxication delirium, persisting dementia, psychotic, mood, anxiety and not otherwise specified disorders), nicotine-related disorders, such as dependence, withdrawal and not otherwise specified disorders, opioid related disorders, including opioid-use disorders (e.g., dependence and abuse disorders) and opioid-induced disorders (e.g., intoxication, withdrawal, intoxication delirium, psychotic, mood, sexual dysfunction, sleep and not otherwise-specified disorders), phencyclidine-related disorders, including phencyclidine-use disorders (e.g., dependence and abuse disorders) and phencyclidine-induced disorders (e.g., intoxication, intoxication delirium, psychotic, mood, anxiety and not otherwise-specified disorders), sedative-, hypnotic- or anxiolytic-related disorders, including sedative-use disorders (e.g., dependence and abuse disorders) and sedative-induced disorders (e.g., intoxication, withdrawal, intoxication delirium, withdrawal delirium, persisting dementia, persisting amnestic, psychotic, mood, anxiety, sexual dysfunction, sleep and not otherwise specified disorders), polysubstance-related disorder, other substance dependence and abuse disorders, and other substance-induced disorders (e.g., intoxication, withdrawal, delirium, persisting dementia, persisting amnestic, psychotic, mood, anxiety, sexual dysfunction, sleep and not otherwise specified disorders); and vision disorders, including glaucoma; comprising administering to the mammal a serotonin reuptake-inhibiting effective amount of a compound of formula (I)

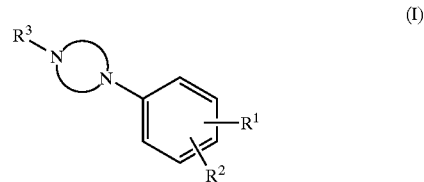

or a pharmaceutically acceptable salt thereof; wherein the group
represents

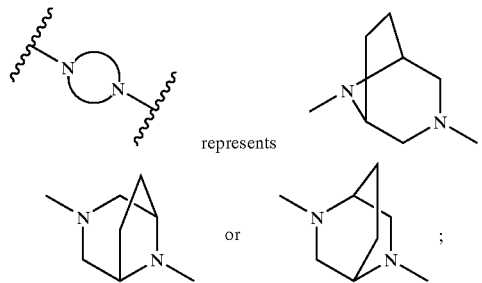

$R^1$ and $R^2$ are selected independently from H, $(C_1-C_6)$ alkyl, $(C_1-C_6)$fluoroalkyl, halogen (e.g., F, Cl, Br, I), cyano, nitro, O—$(C_1-C_6)$alkyl, O—$(C_1-C_6)$fluoroalkyl, —NHC(O)$R^4$ and —O$R^5$, where $R^4$ and $R^5$ are selected independently from H, $(C_1-C_6)$alkyl, and a 5- to 7-membered aryl or heteroaryl ring, or $R^1$ and $R^2$ together with the atoms to which they are attached, form a carbocyclic 5- or 6-membered ring or a heterocyclic 5- or 6-membered ring; and $R^3$ is selected from the group consisting of H, $(C_1-C_6)$ alkyl, $(CH_2)_m$-aryl or $(CH_2)_m$-heteroaryl, wherein m is an integer from 1 to 4, each aryl or heteroaryl group optionally substituted with Cl, Br, CN, $CF_3$, O—$(C_1-C_6)$alkyl, $(C_1-C_6)$alkyl, sulfonyl$(C_1-C_6)$alkyl, —CO$(C_1-C_6)$alkyl, —CONH$_2$, —CONH$(C_1-C_6)$ alkyl, —CON$((C_1-C_6)$alkyl$)_2$, or CH(OH)$(C_1-C_6)$ alkyl.

The present invention further provides a method of treating in a mammal a disease, disorder or condition, as set forth in the preceding paragraph, comprising administering to the mammal an amount of a compound of formula (I), also set forth in the preceding paragraph, or a pharmaceutically acceptable salt thereof effective to treat the disease, disorder or condition.

Further provided herein is a pharmaceutical composition comprising a compound of formula (I) and a pharmaceutically acceptable carrier. Still further provided is a pharmaceutical composition for selectively inhibiting serotonin reuptake in the central nervous system of a mammal, said composition comprising a pharmaceutically acceptable carrier and a serotonin reuptake-inhibiting effective amount of a compound of formula (I).

The present invention also relates to a process for the preparation of a compound of formula (I) comprising the steps of (i) reacting a compound of formula (XI)

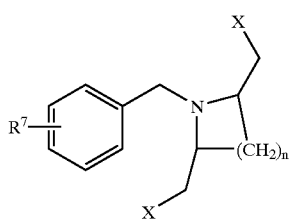

(XI-A)

wherein $R^7$ is H, $(C_1-C_6)$alkyl, or $(C_1-C_6)$alkoxy; X is halo and n is 2; with a compound of formula (IV)

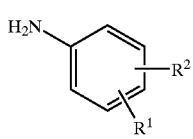

(IV)

wherein $R^1$ and $R^2$ are as defined above; in the presence of a base to provide a mixture of compounds of formulae (XII-A) and (XII-B)

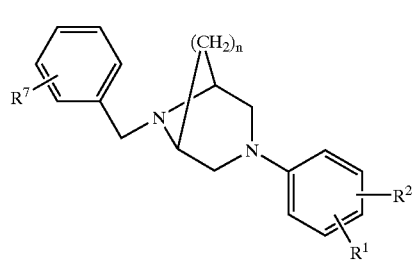

(XII-A)

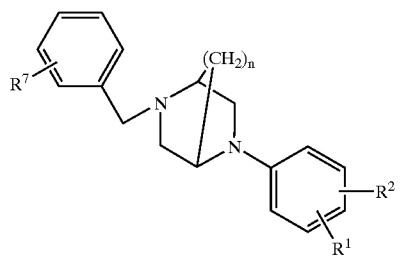

(XII-B)

wherein n, $R^1$ and $R^2$ are as defined above;

(ii) separating the compounds of formulae (XII-A) and (XII-B); and (iii) subjecting each of the compounds of formulae (XII-A) and (XII-B) independently to hydrogenation conditions.

A preferred process of the invention is wherein the base in step (i) is triethylamine or potassium carbonate, more preferably, potassium carbonate. Step (i) is preferably conducted at a temperature ranging from ambient temperature (25° C.) to the reflux temperature of a solvent or a mixture of solvents selected from the group consisting of glyme, diglyme, dimethylformamide, acetonitrile, chloroform, dioxane, acetone, water or lower alcohols (e.g., propanol, ethanol, methanol, etc.), more preferably step (i) is conducted in diglyme at reflux.

Preferred is the process wherein the separation in step (ii) is conducted by chromatographic means, more preferably via silica gel flash chromatography using a polar gradient of solvents, most preferably silica gel flash chromatography employing a polar gradient of ethyl acetate/hexanes. A further preferred embodiment of the invention is wherein the hydrogenation step (iii) is conducted in the in presence of a catalyst selected from the group consisting of palladium on carbon and platinum oxide, more preferably 10% palladium on carbon.

A more preferred process of the invention further comprises the step of reacting the product of step (iii) with a compound of formula $R^{3'}Y$, wherein $R^{3'}$ is selected from $(C_1-C_6)$alkyl, $(CH_2)_m$-aryl or $(CH_2)_m$-heteroaryl, wherein m is an integer from 1 to 4, each aryl or heteroaryl group optionally substituted with Cl, Br, CN, $CF_3$, O—$(C_1-C_6)$ alkyl, $(C_1-C_6)$alkyl, sulfonyl$(C_1-C_6)$alkyl, —CO$(C_1-C_6)$ alkyl, —$CONH_2$, —CONH$(C_1-C_6)$alkyl, —CON$((C_1-C_6)$ alkyl$)_2$, or CH(OH)$(C_1-C_6)$alkyl; and Y is a suitable leaving group. Preferred leaving groups are selected from, e.g., a halide (Cl, Br, or I), tosylate, and mesylate.

Compounds of formula (I) may contain chiral centers, and therefore may exist in different enantiomeric and diastereomeric forms; this invention is directed to all such optical and stereoisomers of compounds of formula (I), as well as mixtures thereof, and to all pharmaceutical compositions and methods of treatment that contain or employ them.

This invention is also directed to isotopically-labeled compounds identical to those recited in formula (I), or pharmaceutically acceptable salts thereof, but for the fact that one or more atoms are replaced therein by an atom having an atomic mass or mass number different from the atomic mass or mass number usually found in nature. Examples of isotopes that can be incorporated into compounds of this invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^1F$ and $^{36}Cl$, respectively.

Compounds of the present invention, prodrugs thereof, and pharmaceutically acceptable salts of said compounds, or of said prodrugs, which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful, for example, in drug and/or substrate tissue distribution assays. Tritiated, i.e., $^3H$, and carbon-14, ie., $^{14}C$, isotopes are particularly preferred for their ease of preparation and detectability. Furthermore, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances.

Isotopically labeled compounds of formula (I) of this invention and prodrugs thereof can generally be prepared by carrying out the procedures set forth below, by substituting a readily available isotopically labeled reagent for a non-isotopically labeled reagent.

In the foregoing description of the invention and throughout this application, the following terms have the stated meanings, unless otherwise indicated: "alkyl" means saturated monovalent hydrocarbon radicals having straight, branched or cyclic moieties, or combinations thereof; "halo" and "halogen" means chloro, fluoro, bromo or iodo; "treating" refers to, and includes, reversing, alleviating, inhibiting the progress of, or preventing a disease, disorder or condition, or one or more symptoms thereof; and, "treatment" and "therapeutically" refer to the act of treating, as defined above.

The term "carbocyclic 5- to 7-member ring," unless otherwise indicated, means any member of cyclopentyl, cyclohexyl, or cycloheptyl monocyclic ring system, with or without at least one point of unsaturation. The term "heterocyclic 5- to 7-membered ring," unless otherwise indicated, means a cyclopentyl, cyclohexyl, or cycloheptyl monocyclic ring system wherein one to three of the carbon atoms is replaced by a nitrogen, oxygen or sulfur atom, with or without one point of unsaturation.

The term "5- to 7-membered aryl ring," unless otherwise indicated, means an unsaturated 5- to 7-membered carbocyclic monocyclic ring system, including but not limited to phenyl. The term "5- to 7-membered heteroaryl ring," unless otherwise indicated, means an unsaturated 5- to 7-membered monocyclic ring system wherein one to three of the ring members is a nitrogen, oxygen or sulfur atom and the remaining ring members are carbon atoms, including but not limited to thienyl, furanyl, pyrrolyl, thiazolyl, oxazolyl, isothiazolyl, isoxazolyl, imidazolyl, pyrimidinyl, and pyridinyl.

The various "diseases, disorders and conditions" to which the compositions and methods of this invention are directed include, without limitation: aggression disorders; anxiety disorders selected from the group consisting of panic attack, agoraphobia, panic disorder with or without agoraphobia, agoraphobia without history of panic disorder, specific phobia, social phobia, obsessive-compulsive disorder, post-traumatic stress disorder and acute stress disorder; cognitive disorders selected from the group consisting of amnestic disorders (e.g., amnestic disorders due to a general medical condition, substance-induced persisting amnestic disorder and amnestic disorders not otherwise specified), deliriums (e.g., deliriums due to a general medical condition, substance-induced delirium and delirium not otherwise specified), dementias (e.g., dementia of the Alzheimer's type, vascular dementia, dementia due to a general medical condition (e.g., AIDS-, Parkinson's-, head trauma-, and Huntington's-induced dementias), substance-induced persisting dementia, dementia due to multiple etiologies, and dementia not otherwise specified) and cognitive disorders not otherwise specified; depression disorders; emesis; epilepsy; food-related behavioral disorders, including anorexia nervosa and bulimia; headache disorders selected from the group consisting of migraine, cluster and vascular headaches; learning disorders, including attention deficit disorder and attention deficit/hyperactivity disorder; obesity; ocular disorders; platelet aggregation disorders; psychotic conditions selected from the group consisting of schizophrenia (e.g., paranoid-type, disorganized-type, catatonic-type, undifferentiated-type and residual-type), schizophreniform disorder, schizoaffective disorder, delusional disorder, brief psychotic disorder, shared psychotic disorder, psychotic disorders due to a general medical condition and psychotic disorders not otherwise specified; sleep disorders selected from the group consisting of primary sleep disorders (e.g., parasomnias and dyssomnias), sleep disorders related to another mental disorder (including, without limitation, mood and anxiety disorders), sleep disorders due to a general medical condition and sleep disorders not otherwise specified; sexual behavior disorders; substance-abuse disorders selected from the group consisting of alcohol-related disorders, including alcohol-use disorders (e.g., dependence and abuse disorders) and alcohol-induced disorders (e.g., intoxication, withdrawal, intoxication delirium, withdrawal delirium, persisting dementia, persisting amnestic, mood, anxiety, sexual dysfunction, sleep and not otherwise specified disorders), amphetamine-related disorders, including amphetamine-use disorders (e.g., dependence and abuse disorders) and amphetamine-induced disorders (e.g., intoxication, withdrawal, intoxication delirium, psychotic, mood, anxiety, sexual dysfunction, sleep and not otherwise-specified disorders), caffeine-related disorders, such as intoxication, induced-anxiety disorder, induced-sleep disorder and disorders not otherwise specified; cannabis-related disorders, including cannabis-use disorders (e.g., abuse and dependence disorders) and cannabis-induced disorders (e.g., intoxication, intoxication delirium, psychotic, anxiety and not otherwise specified disorders), cocaine-related disorders, including cocaine-use disorders (e.g., dependence and abuse disorders) and cocaine-induced disorders (e.g., intoxication, withdrawal, intoxication delirium, psychotic, mood, anxiety, sexual dysfunction, sleep and not otherwise specified disorders), hallucinogen-related disorders, including hallucinogen-use disorders (e.g., dependence and abuse disorders) and hallucinogen-induced disorders (e.g., intoxication, persisting perception, intoxication delirium, psychotic, mood, anxiety and not otherwise specified disorders), inhalant-related disorders, including inhalant-use disorders (e.g., dependence and abuse disorders) and inhalant-induced disorders (e.g., intoxication, intoxication delirium, persisting dementia, psychotic, mood, anxiety and not otherwise specified disorders), nicotine-related disorders, such as dependence, withdrawal and not otherwise specified disorders, opioid related disorders, including opioid-use disorders (e.g., dependence and abuse disorders) and opioid-induced disorders (e.g., intoxication, withdrawal, intoxication delirium, psychotic, mood, sexual dysfunction, sleep and not otherwise-specified disorders), phencyclidine-related disorders, including phencyclidine-use disorders (e.g., dependence and abuse disorders) and phencyclidine-induced disorders (e.g., intoxication, intoxication delirium, psychotic, mood, anxiety and not otherwise-specified disorders), sedative-, hypnotic- or anxiolytic-related disorders, including sedative-use disorders (e.g., dependence and abuse disorders) and sedative-induced disorders (e.g., intoxication, withdrawal, intoxication delirium, withdrawal delirium, persisting dementia, persisting amnestic, psychotic, mood, anxiety, sexual dysfunction, sleep and not otherwise specified disorders), polysubstance-related disorder, other substance dependence and abuse disorders, and other substance-induced disorders (e.g., intoxication, withdrawal, delirium, persisting dementia, persisting amnestic, psychotic, mood, anxiety, sexual dysfunction, sleep and not otherwise specified disorders); vision disorders, including glaucoma; and, various additional diseases, disorders and conditions as well.

"Pharmaceutically acceptable salts" or "pharmaceutically acceptable acid addition salts" of compounds of this invention may be made from those acids which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (i.e., 1,1-methylene-bis-(2-hydroxy-3-naphthoate)) salts.

DETAILED DESCRIPTION OF THE INVENTION

Compounds of formula (I) may be prepared as described below, wherein, unless otherwise indicated, A, $R^1$, $R^2$, $R^3$, $R^4$, $R^5$, $R^6$, $R^7$, and n in the discussion that follows are defined as above. Compounds of the formula (I) may be prepared by processes outline according to the scheme set forth below.

Scheme 1

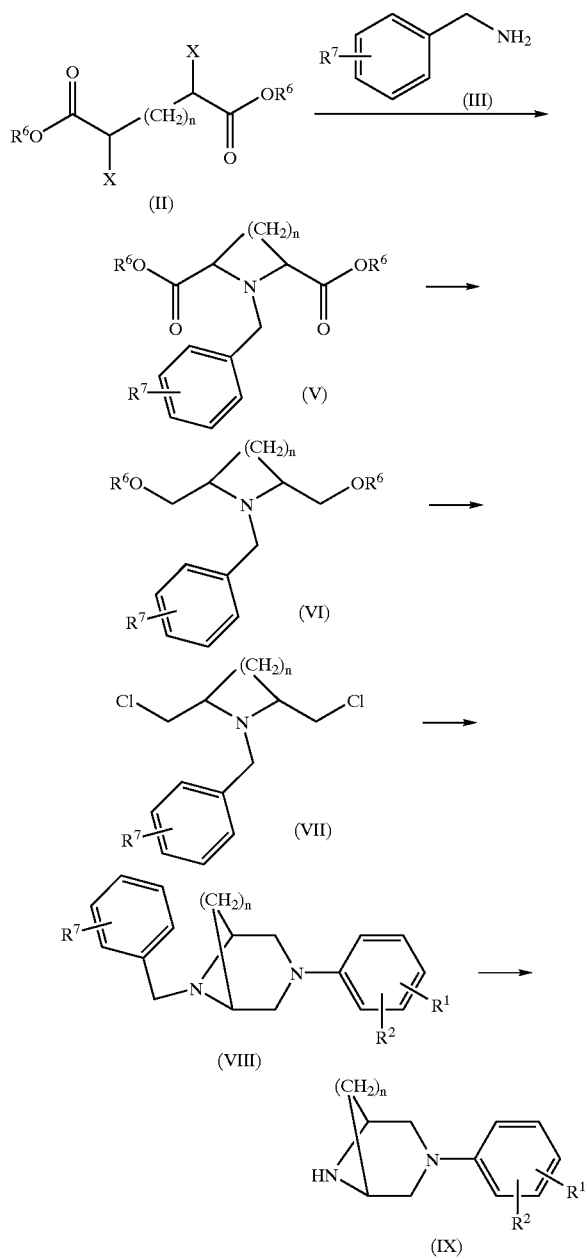
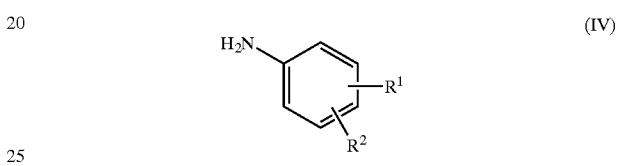

Referring to Scheme I, a compound of general formula (II), wherein $R^6$ is H or $(C_1-C_6)$alkyl, X is halogen (i.e., Br, Cl, or I), and n is 2, is allowed to react with benzylamine (or any other appropriately substituted benzylamine, i.e., by an $R^7$ group where $R^7$ is as define above) in presence of a base, e.g., triethylamine, potassium carbonate, etc., to provide a compound of general formula (V) at a temperature ranging from ambient temperature to the reflux temperature of a solvent or a mixture of solvents selected from the group consisting of dimethylformamide, acetonitrile, chloroform, dioxane, acetone, water, or lower alcohols (e.g., propanol, ethanol, methanol, etc.). The compound of general formula (V) formed in the first step is then transformed into the dio/dialkoxy compound of the formula (VI) in the presence of a reducing agents such as, for example, an aluminum hydride or a borohydride, at a temperature ranging from ambient temperature to the reflux temperature of a solvent or a mixture of solvents selected from the group consisting of lower alkyl alcohols, lower cyclic or acyclic alkyl ethers or dioxane, preferably in the presence of lithium aluminum hydride in THF at ambient (25° C.) temperature. The compound of formula (VI) is then in turn converted into the dichloride compound of formula (VII) via treatment with a reagent, such as, e.g. $SO_2Cl_2$, $POCl_3$ or similar chlorinating reagents, in the absence of a solvent or in a halogenated solvent such as chloroform, carbon tetrachloride or methylene chloride at a temperature ranging from ambient temperature to the reflux temperature of any one of said halogenated solvents or mixtures thereof, preferably conducted with $SO_2Cl_2$ in dioxane at 25° C. The compound of formula (VII) is converted to a compound of formula (VIII) via the reaction of the compound of formula (VII) with excess of an arylamine of the formula:

$$H_2N-\text{Ar}(R^1)(R^2) \quad (IV)$$

wherein $R^1$ and $R^2$ are as defined above, in presence or absence of a solvent, or in a solvent or mixture of solvents selected from diglyme, dimethyl formamide, dioxane, N,N-dimethylacetamide and pyrrolidinone, at a temperature ranging from room temperature to the reflux temperature of any of those solvents or mixtures thereof, preferably in diglyme at reflux. Finally, the compound of general formula (VIII) is then transformed to a compound of formula (IX) by removing the benzyl grouping using hydrogen gas in presence of a catalyst selected from the group consisting of palladium on carbon, platinum oxide or similar reagents in a solvents or mixture of solvents selected from the group consisting of lower cyclic or acyclic alkyl alcohols, lower cyclic or acyclic alkyl ethers, water, acetic acid, formic acid, hydrochloric acid or dimethyl formamide, at a temperature ranging from ambient temperature to the reflux temperatures of said solvent or mixture of solvents, at a hydrogen gas pressure ranging from 0 to 5 atmospheres, preferably conducted with 10% palladium/carbon in 1N HCl/methanol at 1 atmosphere $H_2$.

Compounds of formula (I), wherein $R^3$ is other than H, may be formed by reacting the product of the formula (IX) above with a compound of formula $R^{3'}Y$, wherein $R^{3'}$ is selected from $(C_1-C_6)$alkyl, $(CH_2)_m$-aryl or $(CH_2)_m$-heteroaryl, wherein m is an integer from 1 to 4, each aryl or heteroaryl group optionally substituted with Cl, Br, CN, $CF_3$, O—$(C_1-C_6)$alkyl, $(C_1-C_6)$alkyl, sulfonyl$(C_1-C_6)$alkyl, —CO$(C_1-C_6)$alkyl, —CONH$_2$, —CONH$(C_1-C_6)$alkyl, —CON$((C_1-C_6)$alkyl$)_2$, or CH(OH)$(C_1-C_6)$alkyl; and Y is a suitable leaving group. Suitable leaving groups X are those leaving groups that would be well known to one of skill in the art, e.g., a halide, a tosylate group, mesylate group, etc.

An alternative means for obtaining compounds of formula (I) wherein $R^3$ is other than H is by using a compound of formula $R^{3'}NH_2$ in place of the benzylamine of formula (III) in Scheme I. The use of a compound of formula $R^{3'}NH_2$ avoids the necessity of having to cleave off the protecting benzyl group in Scheme I and replace it with an $R^{3'}$ group. Other variations upon the general synthetic pathway of Scheme I to obtain compounds of formula (I) will be recognized by those of skill in the art.

In Scheme I, the substitution of a compounds of formula (IV) for that of formula (III) and vice-versa, will yield compounds having the substitution at the 3- and 8-positions of the 3,8-diazabicyclo[3.2.1]octane compounds reversed, i.e., compounds wherein the $R^3$ substituent is at the 3-position and the $R^1/R^2$-substituted phenyl group is at the 8-position.

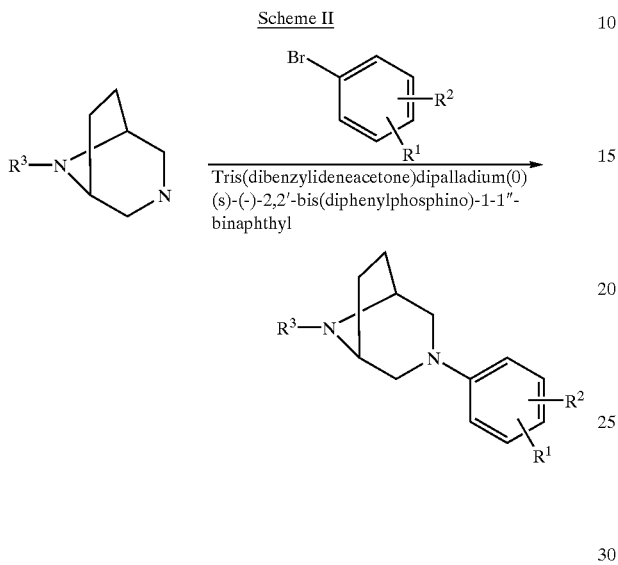

A further alternative means for preparing a 3,8-diazabicyclo[3.2.1]octane compound of formula (I) is found in Scheme II. An already $R^3$-substituted 3,8-diazabicyclo[3.2.1]octane (such compounds may be prepared via protocols analogous to those in U.S. Pat. No. 3,951,980) is reacted with a haloaryl compound in the presence of a dipalladium (0), a phosphine compound, and a base, preferably an akali metal alkoxide, to produce the 3,8-diazabicyclo[3.2.1]octane. The reaction is preferably conducted in the presence of solvent, such as toluene, more preferably in a sealed tube at 50–100° C., most preferably in a sealed tube at 80° C.

Scheme III, below, illustrates a process of obtaining compounds of formula (I) having a 2,5-diazabicyclo[2.2.2]octane ring and/or a diazabicyclo[3.2.1]octane ring. Referring to Scheme III, a compound of general formula (XI) wherein X is halo (Cl, Br, or I) and $R^7$ is as defined above, is allowed to react with an aryl amine of formula (IV), wherein n is 2 and $R^1$ and $R^2$ are as defined above, in the presence of a base, such as triethylamine, potassium carbonate, etc., preferably potassium carbonate, at a temperature ranging from ambient to the reflux temperature of the solvent or a mixture of solvents selected from the group consisting of glyme, diglyme, dimethylformamide, acetonitrile, chloroform, dioxane, acetone, water or lower alcohols (e.g., propanol, ethanol, methanol, etc.), preferably diglyme at reflux, to provide a compound of general formula (XII-A) or (XII-B), respectively. This mixture of isomers may be separated via chromatographic techniques, preferably silica gel flash chromatography using a polar gradient of solvents, preferably silica gel flash chromatography using ethyl acetate/hexanes as solvents to form the gradient.

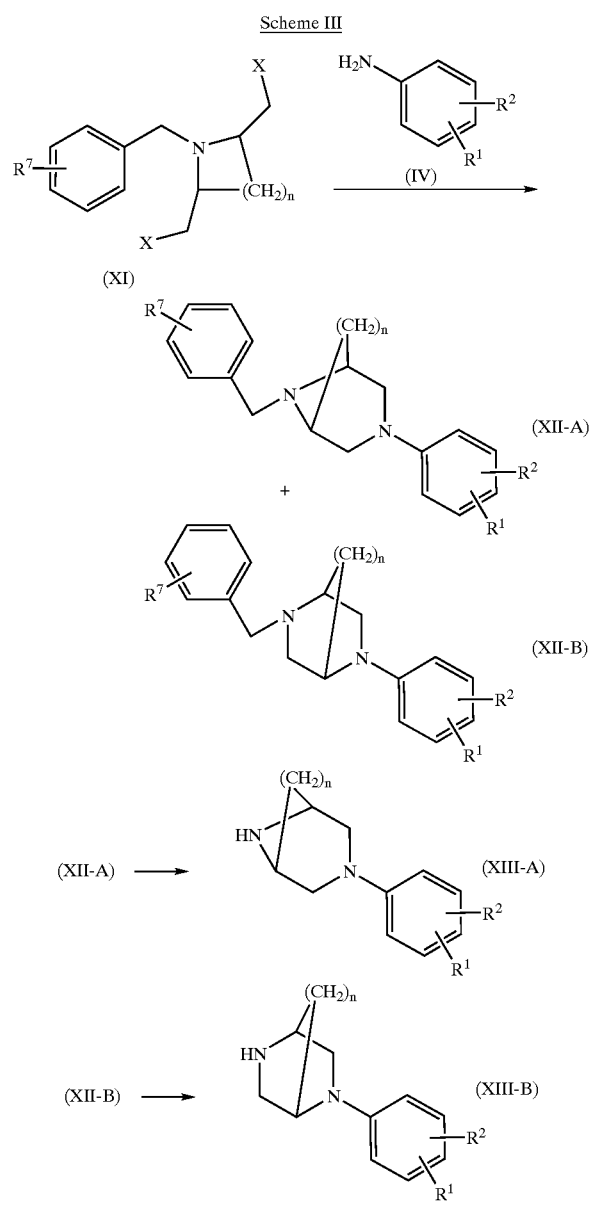

The compounds of formulae (XII-A) and (XII-B), independently after separation, may be transformed to their free base compounds by removing the benzyl group using hydrogen gas in presence of a catalyst selected from the group consisting of palladium on carbon, platinum oxide or similar reagents in a solvent or mixture of solvents selected from the group consisting of lower cyclic or acyclic alkyl alcohols, lower cyclic or acyclic alkyl ethers, water, acetic acid, formic acid, hydrochloric acid or dimethyl formamide, at a temperature ranging from ambient temperature to the reflux temperatures of said solvent or mixture of solvents, at a hydrogen gas pressure ranging from 0 to 5 atmospheres, preferably conducted with 10% palladium/carbon in 1N HCl/methanol at 1 atmosphere $H_2$. Compounds of formula (XIII-A) and (XIII-B) may be transformed into other compounds of formula (I) where $R^3$ is other than hydrogen by means as described above.

The preparation of other compounds of formula (I) not specifically described in the foregoing section can be accom plished using combinations of the reactions described above that will be apparent to those skilled in the art. Furthermore, in each of the reactions discussed or illustrated above, pressure is not critical unless otherwise indicated. Pressures from about 0.5 atmospheres to about 5 atmospheres are generally acceptable, and ambient pressure, i.e., about 1 atmosphere, is preferred, as a matter of convenience.

Those compounds of the invention which are basic in nature are capable of forming a wide variety of different salts with various inorganic and organic acids. Although such salts must be pharmaceutically acceptable for administration to animals, it is often desirable in practice to initially isolate the compound of formula (I) from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids used to prepare the pharmaceutically acceptable acid addition salts of the basic compounds of this invention are those which form non-toxic acid addition salts, i.e., salts containing pharmaceutically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate (i.e., 1,1'-methylene-bis-(2-hydroxy-3-naphthoate)) salts.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

Although such salts must be pharmaceutically acceptable for administration to animals, it is often desirable in practice to initially isolate a compound of the formula (I) from the reaction mixture as a pharmaceutically unacceptable salt, convert the latter back to the free base compound by treatment with an alkaline reagent, and subsequently convert the latter free base to a pharmaceutically acceptable acid addition salt. Such salts are readily prepared by treating the base compound with a substantially equivalent amount of the chosen mineral or organic acid in an aqueous solvent medium, or in a suitable organic solvent, such as methanol or ethanol. Upon careful evaporation of the solvent, the desired solid salt is readily obtained.

The compounds of this invention and their pharmaceutically acceptable salts are useful as selective serotonin reuptake inhibitors. Therefore, said compounds are able to function as therapeutic agents in mammals, including humans, afflicted with various diseases, disorders and conditions, such as those set forth above, characterized by aberrant behavior of the serotonin neurotransmission system.

Serotonin receptor binding affinities of compounds of formula (I) can be determined using standard radioligand binding assays as described in the literature. For example, 5-$HT_{1A}$ receptor binding affinities can be measured using the procedure of Hoyer et al., Brain Res., 376:85 (1986), and 5-$HT_{1D}$ binding affinities can be measured using the procedure of Heuring and Peroutka (J. Neurosci., 7, 894 (1987)); the contents of these documents are incorporated herein by reference.

In vitro binding activity at the 5-$HT_{1D}$ receptor binding site is, for example, determined according to the following procedure. Bovine caudate tissue is homogenized and suspended in 20 volumes of a buffer containing 50 mM TRIS-HCl (tris[hydroxymethyl]aminomethane hydrochloride) at a pH of 7.7, following which the homogenate is centrifuged at 45,000 g for 10 minutes. The resulting supernatant is discarded, and the pellet is resuspended in approximately 20 volumes of 50 mM TRIS-HCl buffer at pH 7.7; said suspension is pre-incubated for 15 minutes at 37° C., after which it is centrifuged again at 45,000 G for 10 minutes. The resulting supernatant discarded, and the pellet (approximately 1 gram) is resuspended in 150 ml of a buffer of 15 mM TRIS-HCl containing 0.01 percent ascorbic acid, final pH 7.7, 10 $\mu$M pargyline and 4 mM calcium chloride ($CaCl_2$)—the suspension is kept on ice at least 30 minutes prior to use.

The inhibitor, control or vehicle is incubated according to the following procedure: to 50 $\mu$l of a 20 percent dimethylsulfoxide (DMSO)/80 percent distilled water solution is added 200 $\mu$l of tritiated 5-hydroxytryptamine (2 nM) in a buffer of 50 mM TRIS-HCl containing 0.01 percent ascorbic acid at pH 7.7, 10 $\mu$M pargyline, 4 mM calcium chloride, 100 nM of 8-hydroxy-DPAT (dipropylaminotetraline) and 100 nM of mesulergine. To this mixture is added 750 $\mu$l of bovine caudate tissue, and the resulting suspension is vortexed to ensure a homogenous suspension; the suspension is then incubated in a shaking water bath for 30 minutes at 25° C.; after incubation is complete, the suspension is filtered using glass fiber filters (eq., Whatman GF/B-filters). The pellet is washed three times with 4 ml of a buffer of 50 mM TRIS-HCl (pH 7.7), and is then placed in a scintillation vial with 5 ml of scintillation fluid (aquasol 2) and allowed to sit overnight. The percent inhibition is calculated for each dose of the compound, and an $IC_{50}$ value is then calculated from the percent inhibition values.

Binding affinities at the 5-$HT_{1A}$ receptor is, for example, determined according to the following procedure. Rat brain cortex tissue is homogenized and divided into samples of 1 g lots and diluted with 10 volumes of 0.32 M sucrose solution. The suspension is then centrifuged at 900 g for 10 minutes, the supernatant separated and recentrifuged at 70,000 g for 15 minutes and the pellets are then collected and resuspended in 10 volumes of 15 mM TRIS-HCl (pH 7.5); the remaining supernatant is discarded. The resulting suspension is allowed to incubate for 15 minutes at 37° C., after which it is then centrifuged at 70,000 g for 15 minutes and the supernatant discarded. The resulting tissue pellet is resuspended in a buffer of 50 mM TRIS-HCl (pH 7.7) containing 4 mM of calcium chloride and 0.01 percent ascorbic acid—this tissue suspension is stored at −70° C. until ready for an experiment.

The tissue can be thawed immediately prior to use, diluted with 10 $\mu$M pargyline and kept on ice; tissue incubation is according to the following procedure. Fifty microliters of control, inhibitor, or vehicle (1 percent DMSO final concentration) is prepared at various dosages. To this solution is added 200 $\mu$l of tritiated 8-hydroxy DPAT at a concentration of 1.5 nM in a buffer of 50 mM TRIS-HCl at pH 7.7, containing 4 mM calcium chloride, 0.01 percent ascorbic acid and pargyline. 750 $\mu$l of tissue is added, the resulting suspension is vortexed to ensure homogeneity, and is then incubated in a shaking water bath for 30 minutes at 37° C. The solution is filtered, and then washed twice with 4 ml of 10 mM TRIS-HCl at pH 7.5 containing 154 mM of sodium chloride.

Agonist and antagonist activities of compounds of formulae (I) at the 5-$HT_{1A}$ and 5-$HT_{1D}$ receptors is, for example, determined using a single saturating concentration according to the following procedure. Male Hartley guinea pigs are decapitated and 5-$HT_{1A}$ receptors are dissected out of the hippocampus, while 5-$HT_{1D}$ receptors are obtained by slicing at 350 mm on a McIlwain tissue chopper and dissecting out the substantia nigra from the appropriate slices. The individual tissues are homogenized in a 5 mM HEPES buffer containing 1 mM EGTA (pH 7.5) using a hand-held glass-Teflon® homogenizer and centrifuged at 35,000 g for 10 minutes at 4° C. The resulting pellets are resuspended in a 100 mM HEPES buffer containing 1 mM EGTA (pH 7.5), to a final protein concentration of 20 mg (hippocampus) or 5 mg (substantia nigra) of protein per tube; the following agents are added so that the reaction mix in each tube contains 2.0 mM $MgCl_2$, 0.5 mM ATP, 1.0 mM cAMP, 0.5 mM IBMX, 10 mM phosphocreatine, 0.31 mg/mL creatine phosphokinase, 100 µM GTP and 0.5–1 microcuries of [$^{32}$P]-ATP (30 Ci/mmol: NEG-003—New England Nuclear). Incubation is initiated by the addition of tissue to siliconized microfuge tubes (in triplicate) at 30° C. for 15 minutes. Each tube receives 20 µl tissue, 10 µl drug or buffer (at 10×final concentration), 10 µl of 32 nM agonist or buffer (at 10×final concentration), 20 µl forskolin (3 µM final concentration) and 40 µl of the preceding reaction mix. Incubation is terminated by the addition of 100 µl 2% SDS, 1.3 mM cAMP, 45 mM ATP solution containing 40,000 dpm [$^3$H]-cAMP (30 Ci/mmol: NET-275—New England Nuclear) to monitor the recovery of cAMP from the columns (the separation of [$^{32}$P]-ATP and [$^{32}$P]-cAMP is accomplished using the method of Salomon et al., *Analytical Biochemistry*, 1974, 58, 541–548, the contents of which are incorporated herein by reference). Radioactivity is quantified by liquid scintillation counting. Maximal inhibition is defined by 10 µM (R)-8-OH-DPAT for 5-$HT_{1A}$ receptors, and 320 nM 5-HT for 5-$HT_{1D}$ receptors. Percent inhibitions by the test compounds are then calculated in relation to the inhibitory effect of (R)-8-OH-DPAT for 5-$HT_{1A}$ receptors or 5-HT for 5-$HT_{1D}$ receptors. The reversal of agonist-induced inhibition of forskolin-stimulated adenylate cyclase activity is calculated in relation to the 32 nM agonist effect.

The compounds of this invention are, for example, tested for in vivo activity for antagonism of 5-$HT_{1D}$ agonist-induced hypothermia in guinea pigs according to the following procedure. Male Hartley guinea pigs from Charles River, weighing 250–275 grams on arrival and 300–600 grams at testing, serve as subjects in the experiment. The guinea pigs are housed under standard laboratory conditions on a 7 a.m. to 7 p.m. lighting schedule for at least seven days prior to experimentation. Food and water are available ad libitum until the time of testing. Compounds of formula (I) are administered, for example, as solutions in a volume of 1 ml/kg; the vehicle used is varied depending on compound solubility. Test compounds are typically administered either sixty minutes orally (p.o.) or 0 minutes subcutaneously (s.c.) prior to administration of a 5-$HT_{1D}$ agonist, such as [3-(1-methylpyrrolidin-2-ylmethyl)-1H-indol-5-yl]-(3-nitropyridin-3-yl)-amine, which can be prepared as described in PCT publication WO 93/11106, published Jun. 10, 1993 (the contents of which are incorporated herein by reference), and which is administered at a dose of 5.6 mg/kg, s.c.

Before a first temperature reading is taken, each guinea pig is placed in a clear plastic shoe box containing wood chips and a metal grid floor and allowed to acclimate to the surroundings for 30 minutes. Animals are then returned to the same shoe box after each temperature reading. Prior to each temperature measurement each animal is firmly held with one hand for a 30-second period. A digital thermometer with a small animal probe is used for temperature measurements. The probe is made of semi-flexible nylon with an epoxy tip. The temperature probe is inserted 6 cm. into the rectum and held there for 30 seconds or until a stable recording is obtained. Temperatures are then recorded.

In p.o. screening experiments, a "pre-drug" baseline temperature reading is made at −90 minutes, the test compound is given at −60 minutes and an additional −30 minute reading is taken. The 5-$HT_{1D}$ agonist is then administered at 0 minutes and temperatures are taken 30, 60, 120 and 240 minutes later. In subcutaneous screening experiments, a pre-drug baseline temperature reading is made at −30 minutes. The test compound and 5-$HT_{1D}$ agonists are given concurrently and temperatures are taken at 30, 60, 120 and 240 minutes later. Data are analyzed with two-way analysis of variants with repeated measures in Newman-Keuls post hoc analysis.

The serotonin 5-$HT_1$ agonist activity can be determined by in vitro receptor binding assay, as described for the 5-$HT_{1A}$ receptor using rat cortex as the receptor source and [$^3$H]-8-OH-DPAT as the radioligand [D. Hoyer et al. *Eur. J. Pharm.*, 118, 13 (1985)] and as described for the 5-$HT_{1D}$ receptor using bovine caudate as the receptor source and [$^3$H]serotonin as the radioligand [R. E. Heuring and S. J. Peroutka, *J. Neuroscience*, 7, 894 (1987)]; the contents of these documents are incorporated herein by reference.

The binding activity at the 5-HT2A receptor is, for example, determined according to the following procedure. Male Sprague-Dawley rats are decapitated and their brains removed. Frontal cortices are dissected and homogenized in 50 mM Tris HCl buffer (pH 7.4 at 4° C.) containing 2 mM $MgCl2$ using a Polytron homogenizer (setting 15,000 rpm). The homogenate is centrifuged for ten minutes at 40,000×g (20,000 rpm in a Sorvall SS34 rotor). The supernatant was discarded and the pellet resuspended with the Polytron homogenizer in fresh ice-cold 50 mM TRIS HCl (pH 7.4 at 4° C.) buffer containing 2 mM $MgCl2$ and centrifuged again. The final pellet was resuspended in 50 mM Tris HCl buffer (pH 7.7 at 22° C.) for a final tissue concentration of 9 mgs wet weight tissue per mL buffer. Incubation is initiated by the addition of tissue to V-bottom polypropylene 96 well plates (in triplicate). Incubation is at 37° C for 15 minutes in a water bath. Each tube receives 200 µL tissue suspension, 25 µL $^3$H-ketanserin (0.4 nM final concentration), and 25 µL drug or buffer. Nonspecific binding is determined using 10 µM cinanserin. Incubation is ended by rapid filtration under vacuum through fire-treated Whatman GF/B glass fiber filters (presoaked in 0.5% polyethenylenimine (PEI) and dried) and rinsed with ice-cold 50 mM Tris HCl buffer (pH 7.7 at 4° C.), setting 555 on a Skatron 96 well harvester. Filters are put into sample bags with 10 mL Betaplate scintillation fluid and allowed to sit 10 minutes before counting on a Betaplate scintillation counter (Wallac).

The binding activity at the $\alpha_1$ receptor is, for example, determined according to the following procedure. Male Sprague-Dawley rats are decapitated and their brains removed. Cortices are dissected and homogenized in 50 mM Tris HCl buffer (pH 7.4 at 4° C.) containing 2 mM $MgCl2$ using a Polytron homogenizer (setting 15,000 rpm). The homogenate is centrifuged for ten minutes at 40,000×g (20,000 rpm in Sorvall SS34 rotor). The supernatant was discarded and the pellet resuspended with the Polytron homogenizer in fresh ice-cold 50 mM TRIS HCl (pH 7.4 at 4° C.) buffer containing 2 mM $MgCl2$ and centrifuged again. The final pellet was resuspended in 50 mM Tris HCl buffer (pH 8.0 at 22° C.) for a final tissue concentration of 12.5 mgs wet weight tissue per mL buffer. Incubation is initiated by the addition of tissue to V-bottom polypropylene 96 well plates (in triplicate). Incubation is at 25° C. for 30 minutes on a shaker. Each tube receives 200 µL tissue suspension, 25 µL 3H-Prazosin (0.2 nM final concentration) and 25 µL drug or buffer. Nonspecific binding is determined using 10 µM phentolamine. Incubation is ended by rapid filtration under vacuum through fire-treated Whatman GF/B glass fiber filters (presoaked in 0.5% PEI and dried) and rinsed with ice-cold 50 mM Tris HCl buffer (pH 7.7 at 4° C.), setting 555 on a Skatron 96 well harvester. Filters are put into sample bags with 10 mL Betaplate scintillation fluid and allowed to sit 10 minutes before counting on a Betaplate scintillation counter (Wallac).

The binding activity at the dopamine $D_2$ receptor is, for example, determined according to the following procedure. Male Sprague-Dawley rats are decapitated and their brains removed. Striata are dissected and homogenized in 50 mM Tris HCl buffer (pH 7.4 at 4° C.) containing 2 mM $MgCl_2$ using a Polytron homogenizer (setting 15,000 rpm). The homogenate is centrifuged for ten minutes at 40,000×g (20,000 rpm in a Sorvall SS34 rotor). The supernatant was discarded and the pellet resuspended with the Polytron in fresh ice-cold 50 mM Tris HCl (pH 7.4 at 4° C.) containing 2 mM $MgCl_2$ buffer and centrifuged again. The final pellet was resuspended in 50 mM Tris HCl buffer containing 100 mM NaCl, 1 mM $MgCl_2$ (pH 7.4 at 37° C.) for a final tissue concentration of 3 mg wet weight tissue per mL buffer. Incubation is initiated by the addition of tissue to V-bottom polypropylene 96 well plates (in duplicate or triplicate). Incubation is at 37° C. for 15 minutes in a heated water bath. Each tube receives 200 µL tissue suspension, 25 µL $^3$H-spiperone (0.2 nM final concentration) and 25 µL drug or buffer. Nonspecific binding is determined using 10 µM (+)-butaclamol. Incubation is ended by rapid filtration under vacuum through fire-treated Whatman GF/B glass fiber filters (presoaked in 0.5% PEI and dried) and rinsed with ice-cold 50 mM Tris HCl buffer (pH 7.7 at 4° C.), setting 555 on the Skatron 96 well harvester (15 sec wash). Filters are dried, put into sample bags with 10 mL Betaplate scintillation fluid and counted on a Betaplate scintillation counter (EG&G/Wallac).

The neurotransmitter uptake activity in rat synaptosomes or HEK-293 cells transfected with the human serotonin, dopamine or norepinephrine transporter is, for example, determined according to the following procedure. For rat synaptosomes preparation, male Sprague Dawley rats are decapitated and the brains removed. The cortex, hippocampi and corpus striata are dissected out and placed in ice cold sucrose buffer, 1 gram in 20 mls (320 mM sucrose containing 1mg/ml glucose, 0.1mM EDTA and brought up to pH 7.4 with Tris base). The tissues are homogenized in a glass homogenizing tube with a teflon pestle at 350 RPMS using a Potters homogenizer. The homogenate is centrifuged at 1000×g for 10 min, at 4 C. The resulting supernatant is re-centrifuged at 17,000×g for 20 min, at 4 C. The final pellet is then resuspended in an appropriate volume of sucrose buffer that yielded less than 10% uptake.

For cell preparation, HEK-293 cells transfected with the human serotonin (5-HT), norepinephrine (NE) or dopamine (DA) transporter were grown in DMEM (Gibco) supplemented with 10% dialyzed FBS (Gibco), 2 mM L-glutamine and 250 µg/ml G418 for the 5-HT and NE transporter or 2 µg/ml puromycin for the DA transporter, for selection pressure. The cells were grown in Gibco triple flasks, harvested with PBS and diluted to an appropriate amount to yield less than 10% uptake.

For the neurotransmitter uptake assay, the uptake assays were conducted in glass tubes containing 50 µL of solvent, inhibitor or 10 µM sertraline, desipramine or nomifensine for the 5-HT, NE or DA assay nonspecific uptake, respectively. Each tube contained 400 µL of [$^3$H]5-HT (5 nM final), [$^3$H]NE (20 nM final) or [$^3$H]DA (5 nM final) made up in modified containing 100 µM pargyline and glucose (1 mg/ml). The tubes were placed on ice, 50 µL of synaptosomes or cells was added to each tube. The tubes were then incubated at 37° C. for the 7 min (5-HT, DA) or 10 min (NE). The incubation was terminated by filtration (GF/B filters), using a 96 well Brandel Cell Harvester, the filters were washed with modified Krebs buffer and either counted in a liquid scintillation counter or in a LKB Beta Plate counter.

Compounds prepared as working examples of the present invention and tested in accordance with the foregoing methods showed good binding activity in the range of more than 50% inhibition at <1000 (one thousand) nM concentration in the serotonin reuptake, dopamine reuptake and norepinephrine reuptake assays.

The compounds of this invention, and their pharmaceutically acceptable salts, can be administered via either the oral, parenteral or topical routes. In general, these compounds are most desirably administered in dosages ranging from about 0.01 to about 250 mg per day, in single or divided doses (e.g., from 1 to 4 doses per day), although variations will necessarily occur depending upon the species, weight and condition of the subject being treated, as well as the particular route of administration chosen. However, a dosage level that is in the range of about 0.07 mg to about 21 mg per kg of body weight per day is most desirably employed. Variations may nevertheless occur depending upon the subject being treated and its individual response to said medicament, as well as on the type of pharmaceutical formulation chosen, and the time period, and interval, at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The compounds of the invention may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants, such as starch (and preferably corn, potato or tapioca starch), alginic acid and certain complex silicates, and granulation binders, such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound of formula (I) in either sesame or peanut oil, or in aqueous propylene glycol, may be employed. The aqueous solutions should be suitably buffered (preferably at a pH of greater than 8), if necessary, and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the active compounds of the present invention topically for the treatment of conditions of the skin; this may be done by way of creams, jellies, gels, pastes, patches, ointments and the like, in accordance with standard pharmaceutical practice.

EXAMPLES

The present invention is illustrated by the following examples. It will be understood, however, that the invention is not limited to the specific details of these examples. Melting points are uncorrected. Proton nuclear magnetic resonance spectra ($^1$H NMR) and $^{13}$C nuclear magnetic resonance spectra ($^{13}$C NMR) are measured using standard techniques. The peak shapes are denoted as follows: s, singlet; d, doublet; t, triplet; q, quartet, m, multiplet, b, broad.

Example 1

3-(4-CHLOROPHENYL)-3,8-DIAZABICYCLO[3.2.1]OCTANE

A. (1-Benzyl-5-hydroxymethyl-pyrrolidine-2-yl)-methanol

A solution of 96.4 grams of 1-benzyl-pyrrolidine-2,5-dicarboxylic acid, 2-ethyl ester, 5-methyl ester in 380 ml of anhydrous tetrahydrofuran is dripped rapidly into a solution of lithium aluminum hydride (437 mmol) in tetrahydrofuran (1.4 liter) at 0° C. After complete addition, the mixture is stirred for 3 hours at ambient temperature and then carefully quenched with 57.8 ml of water followed by 38.6 ml of 10% sodium hydroxide. The mixture is stirred overnight, filtered through Celite, the Celite washed with $CH_2Cl_2$ and the combined filtrate evaporated to provide 67.11 grams of crude (1-benzyl-5-hydroxymethyl-pyrrolidine-2-yl)-methanol.

B. 1-Benzyl-2,5-bis(chloromethyl)-pyrrolidine

To an ice cold solution of 5.0 grams crude (1-benzyl-5-hydroxymethyl-pyrrolidine-2-yl)-methanol in 50 ml dry dioxane are added 8.12 grams $SO_2Cl_2$. The mixture is stirred at ambient temperature for 24 hours and the solvents removed to dryness providing 5.83 grams crude 1-benzyl-2,5-bis(chloromethyl)-pyrrolidine.

C. 8-Benzyl-3-(4-chlorophenyl)-3,8-diazabicyclo[3.2.1]octane

To a suspension of 5.83 grams of 1-benzyl-2,5-bis(chloromethyl)-pyrrolidine in 15 ml. of diglyme is added 2.88 grams of 4-chloroaniline and 3.12 grams of $K_2CO_3$. The mixture is heated to reflux for 5.5 hours and then brought to ambient temperature. Upon addition of 400 ml water, the pH of the mixture is adjusted to 12 by addition of 2N sodium hydroxide. The aqueous layer is extracted with 3×200 ml ethyl acetate, the combined organic layers are washed with 2×400 ml water, 1×400 ml brine, dried over $MgSO_4$ and then concentrated to dryness providing 6.8 grams of an oil. The crude product is purified by flash chromatography on 300 grams $SiO_2$ using as the mobile phase 20% ethyl acetate in hexane. Product-containing fractions are combined and concentrated to dryness providing 1.8 grams of 8-benzyl-3-(4-chlorophenyl)-3,8-diazabicyclo[3.2.1]octane, a white solid. Mp. 115–117° C.

D. 3-(4-Chlorophenyl)-3,8-diazabicyclo[3.2.1]octane

8-Benzyl-3-(4-chlorophenyl)-3,8-diazabicyclo[3.2.1]octane (8.5 g, 27.17 mmol) and 10% palladium on carbon (8.5 g) were combined in 1N hydrochloric acid/methanol (600 ml). The mixture was hydrogenated at atmospheric pressure for 4 hours under hydrogen gas. The reaction was filtered through Celite and the filtrate was concentrated to yield 3-(4-chlorophenyl)-3,8-diazabicyclo[3.2.1]octane hydrochloride (7.0 g, 100%) as an off-white solid. A portion recrystallized from water yielded white crystalline flakes which had the following properties: M.p. 270–275° C.; $^1$H NMR (CDCl$_3$) δ: 9.70 (brd s, 2H), 7.22 (d, J=9.1 Hz, 2H), 6.87 (d, J=8.7 Hz, 2H), 4.06 (brd s, 2H), 3.55 (d, J=11.6 Hz, 2H), 3.12 (d, J=12 Hz, 2H), 2.01–1.79 (m, 4H); IR (KBr): 3969, 3913, 3862, 3739, 3670, 3194, 3094, 2990, 2972, 2947, 2867, 2778, 2748, 2696, 2657, 2609, 2574, 2537, 2500, 2431, 2396, 2384, 2252, 2133, 2092, 2078, 2033, 1991, 1951, 1922, 1903, 1873, 1799, 1750, 1688, 1600, 1570, 1500, 1460, 1421, 1383, 1367, 1344, 1323, 1269, 1252, 1220, 1207, 1165, 1155, 1120, 1099, 1079, 1059, 1012, 1001, 978, 937, 922, 904, 872, 828, 817, 808, 783, 749, 700, 651, 632, 534, 520, 468, 415, 403, (cm$^{-1}$); Elemental Analysis, Calculated for $C_{12}H_{16}ClN_2$: C, 55.61; H, 6.23; N, 10.81; Found: C, 55.35, H, 6.21, N, 10.79.

Example 2

8-BENZYL-3-(4-FLUOROPHENYL)-3,8-DIAZA-BICYCLO[3.2.1]OCTANE AND 2-BENZYL-5-(4-FLUOROPHENYL)-2,5-DIAZA-BICYCLO[2.2.2]OCTANE

1-Benzyl-2,5-bis-chloromethyl-pyrrolidine (10 g, 38.73 mmol), 4-fluoroaniline (4.309, 38.73 mmol) and potassium carbonate (5.35 g, 38.73 mmol) was combined in diglyme (26 ml) and heated at reflux for 15 h. The mixture was cooled to room temperature, diluted with $H_2O$ (200 ml) and extracted with ethyl acetate (5×600 ml). The combined organic layers were washed with $H_2O$ (3×100 ml at pH 12, adjusted with potassium hydroxide), dried over magnesium sulfate and concentrated to a light brown oil. Silica gel flash chromatography using 5% ethyl acetate/hexanes as eluent yielded the less polar component to be 8-Benzyl-3-(4-fluoro-phenyl)-3,8-diaza-bicyclo[3.2.1]octane (2.9 g, 25.2%) as an off white solid which had the following properties: Mp. 100–102° C.; $^1$H NMR CDCl$_3$ δ: 7.40 (d, J=7.5 Hz, 2H), 7.32 (t, J=8.3 Hz, 2H), 7.27–7.22 (m, 1H), 6.92 (t, J=8.3 Hz, 2H), 6.74–6.68 (m, 2H), 3.59 (s, 2H), 3.33–3.26 (m, 2H), 3.25–3.22 (m, 2H), 2.98 (dd, J=1.7 & 8.7 Hz, 2H), 2.08–2.00 (m,2H), 1.84–1.77 (m, 2H). Analysis calculated for $C_{19}H_{21}FN_2$: C, 77.00; H, 7.14; N, 9.45. Found: C, 77.26 H, 7.40; N, 9.44

More polar component from chromatography yielded 2-Benzyl-5-(4-fluoro-phenyl)-2,5-diaza-bicyclo[2.2.2] octane as a tan solid which had the following properties: Mp. 74–76° C.; $^1$H NMR CDCl$_3$ δ: 7.38–7.27 (m, 4H), 6.92 (t, J=8.3 Hz, 2H), 6.57–6.51 (m, 2H), 3.81–3.68 (m, 4H), 3.16 (dd, J=2.0 & 7.9 Hz, 1H), 3.00 (d, J=2.5 Hz, 1H), 2.97 (d, J=2.1 Hz, 1H), 2.95 (t, J=2.5 Hz, 1H), 2.90–2.85 (m, 1H), 2.14–2.05 (m, 1H), 2.00–1.90 (m, 1H), 1.87–1.78 (m, 1H), 1.65–1.56 (m, 1H). Analysis calculated for $C_{19}H_{21}FN_2$: C, 77.00; H, 7.14; N, 9.45. Found: C, 77.22; H, 7.45; N, 9.58.

Example 3

3-(4-FLUOROPHENYL)-3,8-DIAZA-BICYCLO [3.2.1 ]OCTANE

8-Benzyl-3-(4-fluoro-phenyl)-3,8-diaza-bicyclo[3.2.1] octane (2.7 g, 9.11 mmol) was dissolved in 1N hydrochloric acid/methanol (150 mL); 10% palladium on carbon (1.4 g) was then added under nitrogen. A hydrogenation was then carried out at 1 atmosphere for 2 hours. The reaction mixture was then filtered through Celite and concentrated to yield 3-(4-fluorophenyl)-3,8-diazabicyclo[3.2.1]octane, hydrochoride salt (2.2 g, 100%) as a white solid which had the following properties: Mp. 129–131° C.; $^1$H NMR CDCl$_3$ δ: 9.69 (brd s, 1H), 7.07–6.95 (m, 2H), 6.90–6.80 (m, 2H), 4.05 (brd s, 2H), 3.49 (d, J=10.4 Hz, 2H), 3.08 (d, J=11.2 Hz, 2H), 2.00–1.84 (m, 2H).

Example 4

2-(4-FLUOROPHENYL)-2,5-DIAZABICYCLO [2.2.2]OCTANE

2-Benzyl-5-(4-fluorophenyl)-2,5-diazabicyclo[2.2.2] octane (1.1 g, 3.71 mmol) was dissolved in 1N hydrochloric acid/methanol (60 mL); 10% palladium on carbon (0.50 g) was then added under nitrogen. A hydrogenation was then carried out at 1 atmosphere for 2 hours. The reaction mixture was then filtered through Celite and concentrated to yield 2-(4-fluorophenyl)-2,5-diazabicyclo[2.2.2]octane, hydrochoride salt (0.90 g, 100%) as an off-white solid which had the following properties: Mp. 154–156° C.; $^1$H NMR CDCl$_3$ δ: 9.74 (brd s, 1H), 9.67 (brd s, 1H), 7.00 (t, J=9.1 Hz, 2H), 6.68–6.61 (m, 2H), 4.07 (s, 1H), 3.70 (brd s, 1H), 3.63 (d, J=11.2 Hz, 1H), 3.29 (d, J=10.8 Hz, 1H), 3.23 (brd s, 2H), 2.19–2.04 (m, 1H), 1.95–1.83 (m, 1H), 1.81–1.64 (m, 2H).

Example 5

8-(4-CHLOROPHENYL)-3,8-DIAZABICYCLO [3.2.1]OCTANE

A. 1-(4-Chlorophenyl)-pyrrolidine-2,5-dicarboxylic Acid Diethyl Ester

Diethyl meso-2,5-dibromo adipate (5.0 g, 13.89 mmol), 4-chloro-aniline (6.2 g, 48.60 mmol), potassium iodide (0.032 g, 0.193 mmol) were combined and heated at 80° C. for 3 h then 90° C. for ½ h. Mix was cooled, diluted with 6N hydrochloric acid (400 mL) and extracted with ethyl acetate (3×400 mL). The combined organic layers were washed with water (5×200 mL), brine (200 mL), dried with magnesium sulfate and concentrated to yield a mixture of cis and trans 1-(4-Chloro-phenyl)-pyrrolidine-2,5-dicarboxylic acid diethyl ester (4.53 g, 100%) as a brown oil. Oil was used without further purification.

B. [1-(4-chlorophenyl)-5-hydroxymethyl-pyrrolidin-2-yl]-methanol

Lithium aluminum hydride (1.0 M in tetrahydrofuran, 20.7 mL) was added to tetrahydrofuran (68 mL) at 0° C. 1-(4-Chloro-phenyl)-pyrrolidine-2,5-dicarboxylic acid diethyl ester (4.50 g, 13.81 mmol) in tetrahydrofuran (17 mL) was added rapidly dropwise and the mixture was stirred at room temperature for 4 h. Mix was quenched by careful addition of water (2.5 mL) followed by 10% sodium hydroxide (1.7 mL) and stirred for 15 h then filtered through Celite and the cake was washed with ethyl acetate (2×100 mL). The filtrate was dried with magnesium sulfate and concentrated to yield a mixture of cis and trans [1-(4-Chloro-phenyl)-5-hydroxymethyl-pyrrolidin-2-yl]-methanol (3.34 g, 100%) as a golden oil. Oil was used without further purification.

C. 2,5-Bis-chloromethyl-1-(4-chlorophenyl)-pyrrolidine

[1-(4-Chlorophenyl)-5-hydroxymethyl-pyrrolidin-2-yl]-methanol (3.28 g, 13.57 mmol) in dioxane (30 mL) was cooled to 0° C. and thionyl chloride (2.99 mL, 40.98 mmol) was added dropwise which caused the reaction to gum out of solution. Mixture was stirred at room temperature for 2 h which yielded a brown solution. The reaction was evaporated to dryness which yielded cis and trans 2,5-Bis-chloromethyl-1-(4-chlorophenyl)-pyrrolidine as a brown oil (3.73 g, 100%). Oil was used without further purification.

D. 3-Benzyl-8-(4-chlorophenyl)-3,8-diazabicyclo[3.2.1] octane 2,5-Bis-chloromethyl-1-(4-chlorophenyl)-pyrrolidine (3.73 g, 13.57 mmol), potassium carbonate (3.75 g, 27.14 mmol), and benzyl amine (4.45 mL, 40.71 mmol) in diglyme (25 mL) was heated at reflux for 15 h. The reaction mixture was cooled to room temperature, diluted with diethyl ether (600 mL) and washed with water (6×300 mL). The combined organic layers were dried with magnesium sulfate and concentrated to a brown oil. Silica gel flash chromatography using 50% chloroform/hexanes as eluent yielded 3-Benzyl-8-(4-chloro-phenyl)-3,8-diaza-bicyclo[3.2.1]octane (1.0 g, 23.5%) as a golden solid which had the following properties: Mp. 115–117° C.; $^1$H NMR CDCl$_3$ δ: 7.29 (s, 5H), 7.14 (d, J=8.1 Hz, 2H), 6.67 (d, J=8.3 Hz, 2H), 4.08 (brd s, 2H), 3.38 (s, 2H), 2.54–2.42 (m, 4H), 2.08–2.00 (m, 2H), 1.95–1.86 (m,2H).

E. 8-(4-Chlorophenyl)-3,8-diazabicyclo[3.2.1]octane

3-Benzyl-8-(4-chlorophenyl)-3,8-diazabicyclo[3.2.1] octane was subjected to hydrogenation conditions as in Example 1 D above to obtain the title compound.

Example 6

8-METHYL-3-(3-TRIFLUOROMETHYLPHENYL)-3,8-DIAZABICYCLO[3.2.1 ]OCTANE

8-Methyl-3,8-diaza-bicyclo[3.2.1]octane (0.25 g, 1.98 mmol) (see, U.S. Pat. No. 3,951,980), 1-bromo-3-trifluoromethylbenzene (0.22 ml, 1.80 mmol), tris (dibenzylideneacetone)dipalladium(0)(0.016 g, 0.018 mmol),(s)-(-)-2,2'-bis(diphenylphosphino)-1-1"-binaphthyl (0.011 g, 0.014 mmol), sodium tert-butoxide (0.24 g, 2.52 mmol) and toluene (5 ml) were combined in a sealed tube and heated at 80° C. for 15 hours. The reaction was cooled to room temperature, diluted with water (100 ml) and extracted with ethyl acetate (3×100 ml). The combined organic layer was washed with water (1×100 ml), dried with magnesium sulfate and evaporated to a brown oil. Silica gel flash chromatography using 5% methanol/chloroform as the eluent yielded 8-methyl-3-(3-trifluoromethylphenyl)-3,8-diazabicyclo[3.2.1]octane (0.15g, 30.8% yield) as a golden oil. The oil was dissolved in 1N hydrochloric acid/methanol (30 mL) and concentrated to yield the hydrochloride salt as a pale yellow foam. $^1$H NMR DMSO-d$_6$ δ: 11.30 (s, 1H), 7.41 (t, J=8.3 Hz, 1H), 7.20–7.03 (m, 3H), 4.02 (brd s, 2H), 3.75 (d, J=12.9 Hz, 2H),3.37 (d, J=12.0 Hz, 2H), 2.69 (d, J=5.0 Hz, 3H), 2.22–2.09 (m, 2H), 1.99–1.89 (m, 2H).

Example 7

The following compounds may be prepared in a similar manner to that used in Example 1–6 using the appropriately substituted aryl compound as starting material in place of 4-chloroaniline or 4-fluoroaniline:

3-(3,4-dichlorophenyl)-3,8-diazabicyclo[3.2.1]octane;
3-(2,4-dimethylphenyl)-3,8-diazabicyclo[3.2.1]octane;
3-(4-trifluoromethylphenyl)-3,8-diazabicyclo[3.2.1]octane;
3-(3-fluorophenyl)-3,8-diazabicyclo[3.2.1]octane;
8-p-tolyl-3,8-diazabicyclo[3.2.1]octane; 3-(p-tolyl)-3,8-diazabicyclo[3.2.1]octane;
8-(3,4-dichlorophenyl)-3,8-diazabicyclo[3.2.1]octane;
8-phenyl-3,8-diazabicyclo[3.2.1]octane;
8-(2,4-dimethylphenyl)-3,8-diazabicyclo[3.2.1]octane;
8-(4-fluorophenyl)-3,8-diazabicyclo[3.2.1]octane;
8-(4-trifluoromethylphenyl)-3,8-diazabicyclo[3.2.1]octane;
8-(3,4-fluorophenyl)-3,8-diazabicyclo[3.2.1]octane;
8-benzyl-3-(4-chlorophenyl)-3,8-diaza-bicyclo[3.2.1]octane;
2-benzyl-5-(4-chlorophenyl)-2,5-diaza-bicyclo[2.2.2]octane;
8-ethyl-3-(4-chlorophenyl)-3,8-diaza-bicyclo[3.2.1]octane;
2-ethyl-5-(4-chlorophenyl)-2,5-diaza-bicyclo[2.2.2]octane;
8-methyl-3-(4-chlorophenyl)-3,8-diaza-bicyclo[3.2.1]octane;
2-methyl-5-(4-chlorophenyl)-2,5-diaza-bicyclo[2.2.2]octane;
8-ethyl-3-(3,4-dichlorophenyl)-3,8-diaza-bicyclo[3.2.1]octane;
2-ethyl-5-(3,4-dichlorophenyl)-2,5-diaza-bicyclo[2.2.2]octane;
8-methyl-3-(3,4-dichlorophenyl)-3,8-diaza-bicyclo[3.2.1]octane;
2-methyl-5-(3,4-dichlorophenyl)-2,5-diaza-bicyclo[2.2.2]octane;
8-ethyl-3-(4-methylphenyl)-3,8-diaza-bicyclo[3.2.1]octane;
2-ethyl-5-(4-methylphenyl)-2,5-diaza-bicyclo[2.2.2]octane;
8-methyl-3-(4-methylphenyl)-3,8-diaza-bicyclo[3.2.1]octane;
2-methyl-5-(4-methylphenyl)-2,5-diaza-bicyclo[2.2.2]octane;
3-benzyl-8-(4-chlorophenyl)-3,8-diaza-bicyclo[3.2.1]octane;
3-methyl-8-(4-chlorophenyl)-3,8-diaza-bicyclo[3.2.1]octane;
3-propyl-8-(4-chloro-phenyl)-3,8-diaza-bicyclo[3.2.1]octane;
3-(2-naphthyl)-3,8-diazabicyclo[3.2.1]octane;
3-(1-naphthyl)-3,8-diazabicyclo[3.2.1]octane;
3-(2-isoquinolyl)-3,8-diazabicyclo[3.2.1]octane
8-(2-naphthyl)-3,8-diazabicyclo[3.2.1]octane;
8-(1-naphthyl)-3,8-diazabicyclo[3.2.1]octane
8-(2-isoquinolyl)-3,8-diazabicyclo[3.2.1]octane
2-(4-chlorophenyl)-2,5-diaza-bicyclo[2.2.2]octane;

What is claimed is:

1. A compound of formula (I):

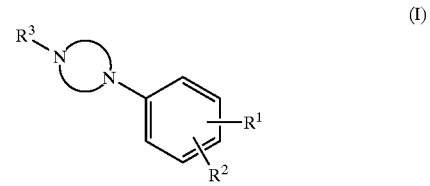

(I)

or pharmaceutically acceptable salts thereof, wherein the group

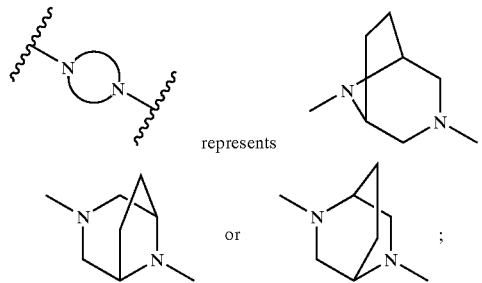

represents $R^1$ and $R^2$ are selected independently from H, (C$_1$–C$_6$) alkyl, (C$_1$–C$_6$)fluoroalkyl, F, Cl, W, I, cyano, nitro, O—(C$_1$–C$_6$)alkyl, O—(C$_1$–C$_6$)fluoroalkyl, —NHC(O)R$^4$ and —OR$^5$, where R$^4$ and R$^5$ are selected independently from H, (C$_1$–C$_6$)alkyl, and a 5- to 7-membered aryl or heteroaiyl ring, or R$^1$ and R$^2$ together with the atoms to which they are attached, form a carbocyclic 5- or 6-membered ring or a heterocyclic 5- or 6-membered ring; and $R^3$ is selected from the group consisting of H, (C$_1$–C$_6$) alkyl, (CH$_2$)$_m$-aryl or (CH$_2$)$_m$-heteroaryl, wherein m is an integer from 1 to 4, each aryl or heteroaryl group optionally substituted with Cl, Br, CN, CF$_3$, O—(C$_1$–C$_6$)alkyl, (C$_1$–C$_6$)alkyl, sulfonyl(C$_1$–C$_6$)alkyl, —CO(C$_1$–C$_6$)alkyl, —CONH$_2$, —CONH(C$_1$–C$_6$)alkyl, —CON((C$_1$–C$_6$)alkyl)$_2$, or CH(OH)(C$_1$–C$_6$)alkyl;

with the proviso that neither R$^1$ nor R$^2$ can be H or methyl, when R$^3$ is H or —(CH$_2$)$_m$-phenyl and when

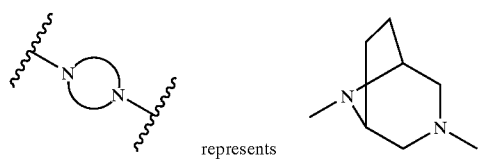

represents

-continued

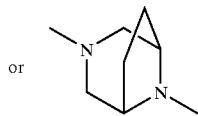

neither R¹ nor R² can be H or methyl when R³ is methyl.

2. A compound according to claim 1 wherein

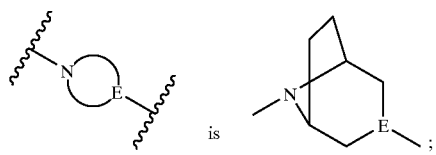

R³ is H or (C₁–C₆)alkyl; and
R¹ and R² are independently chosen from the group consisting of H, halogen, —CF₃, (C₁–C₆)alkyl, —OCH₃, and OCF₃.

3. A compound according to claim 1 wherein R³ is H and R¹ and R² are independently chosen from the group consisting of Cl, —CF₃, (C₁–C₆)alkyl, —OCH₃, and OCF₃.

4. A compound according to claim 1 selected from the group consisting of:

3-(4-chlorophenyl)-3,8-diazabicyclo[3.2.1]octane;
3-(3,4-dichlorophenyl)-3,8-diazabicyclo[3.2.1]octane;
3-(2,4-dimethylphenyl)-3,8-diazabicyclo[3.2.1]octane;
3-(4-fluorophenyl)-3,8-diazabicyclo[3.2.1]octane;
3-(4-trifluoromethylphenyl)-3,8-diazabicyclo[3.2.1]octane;
3-(3-fluorophenyl)-3,8-diazabicyclo[3.2.1]octane;
8-(4-chlorophenyl)-3,8-diazabicyclo[3.2.1]octane;
8-p-tolyl-3,8-diazabicyclo[3.2.1]octane;
3-(p-tolyl)-3,8-diazabicyclo[3.2.1]octane;
8-(3,4-dichlorophenyl)-3,8-diazabicyclo[3.2.1]octane;
8-phenyl-3,8-diazabicyclo[3.2.1]octane;
8-(2,4-dimethylphenyl)-3,8-diazabicyclo[3.2.1]octane;
8-(4-fluorophenyl)-3,8-diazabicyclo[3.2.1]octane;
8-(4-trifluoromethylphenyl)-3,8-diazabicyclo[3.2.1]octane;
8-(3-fluorophenyl)-3,8-diazabicyclo[3.2.1]octane;
8-benzyl-3-(4-fluorophenyl)-3,8-diaza-bicyclo[3.2.1]octane;
2-benzyl-5-(4-fluorophenyl)-2,5-diaza-bicyclo[2.2.2]octane;
8-benzyl-3-(4-chlorophenyl)-3,8-diaza-bicyclo[3.2.2]octane;
2-benzyl-5-(4-chlorophenyl)-2,5-diaza-bicyclo[2.2.2]octane;
8-ethyl-3-(4-chlorophenyl)-3,8-diaza-bicyclo[3.2.1]octane;
2-ethyl-5-(4-chlorophenyl)-2,5-diaza-bicyclo[2.2.2]octane;
8-methyl-3-(4-chlorophenyl)-3,8-diaza-bicyclo[3.2.1]octane;
2-methyl-5-(4-chlorophenyl)-2,5-diaza-bicyclo[2.2.2]octane;
8-ethyl-3-(3,4-dichlorophenyl)-3,8-diaza-bicyclo[3.2.1]octane;
2-ethyl-5-(3,4-dichlorophenyl)-2,5-diaza-bicyclo[2.2.1]octane;
8-methyl-3-(3,4-dichlorophenyl)-3,8-diaza-bicyclo[3.2.1]octane;
2-methyl-5-(3,4-dichlorophenyl)-2,5-diaza-bicyclo[2.2.2]octane;
8-ethyl-3-(4-methylphenyl)-3,8-diaza-bicyclo[3.2.1]octane;
2-ethyl-5-(4-methylphenyl)-2,5-diaza-bicyclo[2.2.2]octane;
8-methyl-3-(4-methylphenyl)-3,8-diaza-bicyclo[3.2.1]octane;
2-methyl-5-(4-methylphenyl)-2,5-diaza-bicyclo[2.2.1]octane;
8-benzyl-8-(4-chlorophenyl)-3,8-diaza-bicyclo[3.2.1]octane;
3-methyl-8-(4-chlorophenyl)-3,8-diaza-bicyclo[3.2.1]octane;
3-propyl-8-(4-chloro-phenyl)-3,8-diaza-bicyclo[3.2.1]octane;
3-(2-naphthyl)-3,8-diazabicyclo[3.2.1]octane;
3-(1-naphthyl)-3,8-diazabicyclo[3.2.1]octane;
3-(2-isoquinolyl)-3,8-diazabicyclo[3.2.1]octane;
8-(2-naphthyl)-3,8-diazabicyclo[3.2.1]octane;
8-(2-naphthyl)-3,8-diazabicyclo[3.2.1]octane;
8-(2-isoquinolyl)-3,8-diazabicyclo[3.2.1]octane;
2-(4-chlorophenyl)-2,5-diaza-bicyclo[2.2.2]octane;
8-methyl-3-(3-trifluoromethylphenyl)-3,8-diazabicyclo[3.2.1]octane;
2-(4-fluorophenyl)-2,5-diazabicyclo[2.2.2]octane;
or pharmaceutically acceptable salts thereof.

5. A method of treating anxiety or depression in a patient in need thereof comprising administering to the patient an effective amount of a compound of formula (I) according to claim 1.

6. A pharmaceutical composition comprising a compound according to claim 1 and a pharmaceutically acceptable carrier.

7. A process for the preparation of a compound of formula (I)

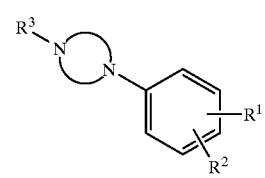

wherein the group

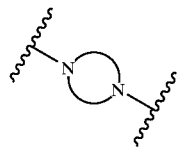 represents 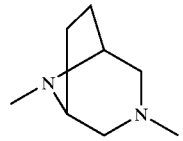

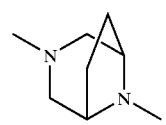 or 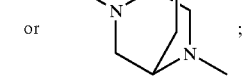 ;

R¹ and R² are selected independently from H, (C¹–C⁶) alkyl, (C₁–C₆)fluoroalkyl, F, Cl, Br, I, cyano, nitro, O—(C$_1$–C$_6$)alkyl, O—(C$_1$–C$_6$)fluoroalkyl, —NHC(O)R$^4$ and —OR$^5$, where R$^4$ and R$^5$ are selected independently from H, (C$_1$–C$_6$)alkyl, and a 5- to 7-membered aryl or heteroaryl ring, or R$^1$ and R$^2$ together with the atoms to which they are attached, form a carbocyclic 5- or 6-membered ring or a heterocyclic 5- or 6-membered ring; and R$^3$ is selected from the group consisting of H, (C$_1$–C$_6$) alkyl, (CH$_2$)$_m$-aryl or (CH$_2$)$_m$-heteroaryl, wherein m is an integer from 1 to 4, each aryl or heteroaryl group optionally substituted with Cl, Br, CN, CF$_3$, O—(C$_1$–C$_6$)alkyl, (C$_1$–C$_6$)alkyl, sulfonyl(C$_1$–C$_6$)alkyl, —CO(C$_1$–C$_6$)alkyl, —CONH$_2$, —CONH(C$_1$–C$_6$)alkyl, —CON((C$_1$–C$_6$)alkyl)$_2$, or CH(OH)(C$_1$–C$_6$)alkyl;

with the proviso that neither R$^1$ nor can be H or methyl, when R$^3$ is H or —(CH$_2$)$_m$-phenyl and when

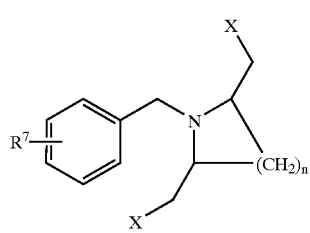

represents

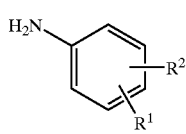

or neither R$^1$ nor R$^2$ can be H or methyl when R$^3$ is methyl; comprising the steps of (i) reacting a compound of formula (XI)

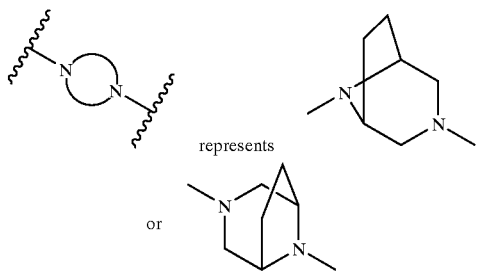

(XI-A)

wherein R$^7$ is H, (C$_1$–C$_6$)alkyl, or (C$_1$–C$_6$)alkoxy; X is halo and n is 2; with a compound of formula (IV)

(IV)

H$_2$N—[phenyl with R$^2$ and R$^1$]

wherein R$^1$ and R$^2$ are selected independently from H, (C$_1$–C$_6$)alkyl, (C$_1$–C$_6$)fluoroalkyl, F, Cl, Br, I, cyano, nitro, O—(C$_1$–C$_6$)alkyl, O—(C$_1$–C$_6$)fluoroalkyl, —NHC(O)R$^4$ and —OR$^5$, where R$^4$ and R$^5$ are selected independently from H, (C$_1$–C$_6$)alkyl, and a 5- to 7-membered aryl or heteroaryl ring, or R$^1$ and R$^2$ together with the atoms to which they are attached, form a carbocyclic 5- or 6-membered ring or a heterocyclic 5- or 6-membered ring; in the presence of a base to provide a mixture of compounds of formulae (XII-A) and (XII-B)

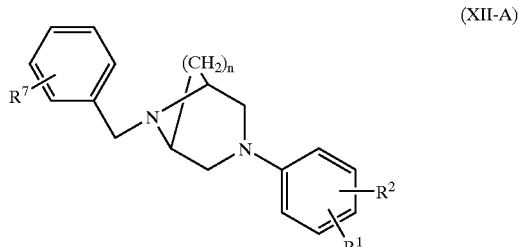

(XII-A)

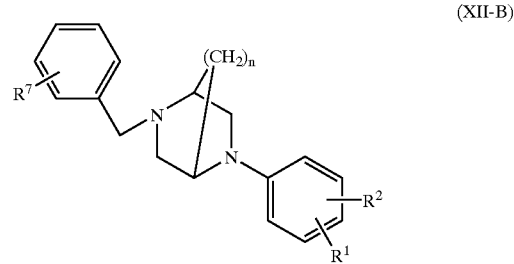

(XII-B)

wherein n, R$^1$ and R$^2$ are as defined above;

(ii) separating chromatographically the compounds of formulae (XII-A) and (XII-B); and (iii) subjecting each of the compounds of formulae (XII-A) and (XII-B) independently to hydrogenation of conditions.

8. A process according to claim 7 wherein the base in step (i) is triethylamine or potassium carbonate.

9. A process according to claim 7 wherein the chromatographic separation of step (ii) is conducted via silica gel flash chromatography using a polar gradient of solvents.

10. A process according to claim 7 wherein the hydrogenation step (iii) is conducted in the in presence of a catalyst selected from the group consisting of palladium on carbon and platinum oxide.

11. A process according to claim 7 further comprising the step of reacting the product of step (iii) with a compound of formula R$^{3'}$Y, wherein R$^{3'}$ is selected from (C$_1$–C$_6$)alkyl, (CH$_2$)$_m$-aryl or (CH$_2$)$_m$-heteroaryl, wherein m is an integer from 1 to 4, each aryl or heteroaryl group optionally substituted with Cl, Br, CN, CF$_3$, —O—(C$_1$–C$_6$)alkyl, (C$_1$–C$_6$)alkyl, sulfonyl(C$_{1-C6}$)alkyl, —CO(C$_1$–C$_6$)alkyl, —CONH$_2$, —CONH(C$_1$–C$_6$)alkyl, —CON((C$_1$–C$_6$)alkyl)$_2$, or CH(OH)(C$_1$–C$_6$)alkyl; and Y is a suitable leaving group.

12. A process according to claim 11 wherein the leaving group is selected from a halide tosylate and mesylate.

* * * * *